US012765988B2

(12) United States Patent
Spenciner

(10) Patent No.: US 12,765,988 B2
(45) Date of Patent: Oct. 20, 2026

(54) SELF-DEPLOYING TISSUE AUGMENTATION PATCHES FOR USE IN SOFT TISSUE REPAIR

(71) Applicant: MEDOS INTERNATIONAL SARL, Le Locle (CH)

(72) Inventor: David B. Spenciner, North Attleboro, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 752 days.

(21) Appl. No.: 18/117,272

(22) Filed: Mar. 3, 2023

(65) Prior Publication Data

US 2024/0293221 A1 Sep. 5, 2024

(51) Int. Cl.
*A61F 2/08* (2006.01)

(52) U.S. Cl.
CPC ..... *A61F 2/0811* (2013.01); *A61F 2002/0852* (2013.01)

(58) Field of Classification Search
CPC .. A61F 2/0811; A61F 2002/0852; A61F 2/08; A61F 2002/0888; A61B 17/04; A61B 2017/0495
See application file for complete search history.

(56) References Cited

U.S. PATENT DOCUMENTS 5,397,331 A 3/1995 Himpens et al.
5,514,378 A 5/1996 Mikos et al.
8,562,633 B2 10/2013 Cully et al.
8,608,651 B2 12/2013 Shluzas
8,613,763 B2 12/2013 Pavonik et al.
8,870,915 B2 10/2014 Mayer et al.
9,345,567 B2 5/2016 Sengun
10,045,851 B2 8/2018 Grotz
(Continued)

FOREIGN PATENT DOCUMENTS

EP 0464163 B1 4/1995
WO 2021061984 A2 4/2021

OTHER PUBLICATIONS

Labbé, Marc R. "Arthroscopic technique for patch augmentation of rotator cuff repairs." Arthroscopy: The Journal of Arthroscopic & Related Surgery 22.10 (2006): 1136-e1.

*Primary Examiner* — Yashita Sharma
(74) *Attorney, Agent, or Firm* — Barnes & Thornburg LLP

(57) ABSTRACT

Self-deploying devices, systems, and methods of use to improve both the reliability of soft tissue repair procedures and the speed at which the procedures are completed are provided. The devices and systems include one or more surgical implants that include a sheet of biocompatible or bioabsorbable material that can be positioned as an implant within a patient's body, the sheet of material being introduced into the patient's body in a mechanically compressed or folded or rolled form. The sheet of material can include a self-expanding ring or framework that resiliently biases the sheet of material to open into a flat sheet once mechanically released within the patient's body. The sheet of material can be used for performing a surgical repair by attaching the deployed sheet to tissue within the body. The surgical repair can comprise an orthopedic repair or a muscular repair. In some examples, the self-expanding ring or framework is removable after the sheet of material is implanted.

23 Claims, 16 Drawing Sheets

(56) References Cited

U.S. PATENT DOCUMENTS

| | | | |
|---|---|---|---|
| 10,278,801 B2 | 5/2019 | Kucklick | |
| 10,449,027 B2 | 10/2019 | Griffin et al. | |
| 10,702,383 B2 | 7/2020 | Cao et al. | |
| 10,912,579 B2 | 2/2021 | Kucklick | |
| 2002/0010457 A1* | 1/2002 | Duchon ................ | A61F 2/0063 600/407 |
| 2004/0019360 A1 | 1/2004 | Farnsworth et al. | |
| 2011/0011407 A1 | 1/2011 | Townsend et al. | |
| 2011/0152897 A1* | 6/2011 | Bates ............... | A61B 17/00234 606/151 |
| 2019/0274814 A1 | 9/2019 | Euteneuer et al. | |
| 2021/0330438 A1 | 10/2021 | Bailly et al. | |

* cited by examiner 100
111
(on top)
130
112
(underneath)

100
111
182
121
130
170
193
112
122
183

100
101
191
121
181
120
130
102
192

SELF-DEPLOYING TISSUE AUGMENTATION PATCHES FOR USE IN SOFT TISSUE REPAIR

FIELD

The present disclosure relates to systems, devices, and methods for securing soft tissue to bone, and more particularly relates to systems, devices, and methods that increase the area of coverage and/or compression between suture filament and tissue during procedures like rotator cuff repairs.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to degenerated tissue leading to inadequate suture-to-anchor fixation and further damage to the soft tissue.

Repair constructs made from one or more surgical filaments are typically used in soft tissue repair procedures, e.g., rotator cuff fixations, to secure the tissue in a desired location. The repair constructs are typically disposed through one or more portions of the tissue to be repaired, which can cause trauma to the tissue, and are often coupled to anchors disposed in bone to which the tissue is to be approximated. Further, in situations where the soft tissue has already begun to degenerate, the added pressure applied by the sutures can cause further damage to the tissue, for instance by causing abrasion of the tissue or "cheese-wiring," which refers to one or more strings of tissue peeling away from the main tissue like a string of cheese peels away from a cheese block when a wire cheese slicer is used to separate cheese from the block. In other words, because the suture has a small surface area, and a significant amount of force is being applied to the soft tissue over the small surface area of the tissue, the suture may have a tendency to cut into the already compromised tissue, thus causing further damage. Currently available solutions to this problem include the application of a relatively large formation of allograft or xenograft, typically about 3 centimeters by about 3 centimeters, to the soft tissue after the repair has been performed but prior to tightening the soft tissue down with the suture. The application of the formation, however, is often expensive, necessitates many sutures, and requires a high skill level to operate and is thus used by only a select few surgeons. Further, the application of the relatively large formation can add a significant amount of time to a surgical procedure, on the order of an additional half hour to one hour per allograft or xenograft formation applied. Still further, in certain forms of repair constructs, such as those that include a membrane that provides strength to the repair construct, it can be difficult for a surgeon to ensure a preferred side of the repair construct is in contact with the host tissue.

Additionally, repair constructs, such as patches or scaffolds as provided for herein, can sometimes be cumbersome to deliver. The delivery occurs through a small opening or cannula, often causing the construct to be deformed prior to and/or during insertion to the surgical site. Existing repair operations can involve delivery of a tissue augmentation patch or scaffold though a small opening or cannula into the surgical region. Passing the tissue augmentation patch though the small opening can be very difficult and often requires the tissue augmentation patch to be deformed prior to or during insertion.

One of the biggest challenges of superior capsular reconstruction (SCR) surgery in the shoulder is bringing the patch into the sub-acromial space where it can be attached to the humerus, cuff remnant, and/or glenoid rim. Various methods have been described previously for deploying a patch into the shoulder, starting with effectively mashing a patch up into a ball to be jammed through a cannula in hope of unfurling it successfully once fully in the surgical site, but also including dragging the patch into the shoulder with curved forceps. More recently, a variety of methods have been described where the graft is folded or rolled up, passed through a cannula, and then unfolded or unrolled for attachment to the rotator cuff. Techniques for rolling and unrolling work better than the merely stuffing the patch into the joint, however, in all existing cases, a complex deployment instrument must be employed, which offers the potential for an improved design. Many of these existing alternative patch deployment methods are complex and/or expensive. The clinical need therefore is a patch that is either self-deploying or nearly so.

It is therefore desirable to provide systems, devices, and methods for use in soft tissue repair that are robust, strong, and promote healing, yet minimize the costs and time of the procedure and provide for easier delivery of surgical repair constructs provided for herein (e.g., self-deploying or nearly-self-deploying patches) to the surgical site.

SUMMARY

Systems, devices, and methods are generally provided for performing surgical procedures involving sutures, such as rotator cuff repairs, among other suture repair procedures. More specifically, the systems, devices, and methods are designed to allow a user to introduce a folded or otherwise reduced in overall size tissue augmentation construct (e.g., a patch) into a surgical site and subsequently initiate self-deployment of the patch that expands the overall coverage of the patch increases before the patch is secured in place to tissue. The tissue augmentation constructs, which come in a variety of configurations, can also be used to expand a footprint of the sutures with which they are associated. The expanded footprint helps distribute force applied by the suture on the tissue across a greater surface area, can protect aspects of the system and/or tissue, provide bulk to otherwise compromised or degenerate tissue and/or tendon, and/or can help promote tissue growth and repair at the surgical site.

The present disclosure describes systems, methods, and devices for deploying a graft onto an interior region of the body. In some examples, a self-deploying implant or graft can transition between a first state and a second state, in which the graft, in the first state, is smaller in at least one dimension than in the second state, in which the graft is larger in at least one dimension. One advantage of this dual-state is to facilitate passage of this graft into the body in the first state and then reassemble or deploy the graft into the second state in preparation for subsequent attachment to a soft tissue repair site.

Examples of the present disclosure include self-deploying grafts that include one or more flexible resilient members (e.g., a nitinol wire ring) embedded on or about the periphery of a graft. In some examples, the one or more flexible resilient members, in a first state, are twisted and/or folded onto itself such that the one or more flexible resilient members and the material associated with the one or more flexible resilient members (e.g., a tissue augmentation construct, patch, or graft) form two, three, four, or more smaller rings that are stacked on top of each other. In this first state, for example, the overall size (e.g., width or diameter) of the stacked graft is substantially less than in a second state where the one or more flexible resilient members are untwisted and/or unfolded. Therefore, examples of the self-deploying grafts disclosed herein are advantageously able to be inserted in their smaller, first state, and thereby improve their ability to be inserted into a surgical site (e.g., through a cannula) and/or increase the ultimate size of the graft in the surgical site when deployed into the second state after insertion into the surgical site. However, this use of smaller configurations is different from previously existing delivery techniques because the self-deploying grafts are specifically designed to be more compact in delivery and self-deploy in a particular manner. This is different from just folding or rolling up a graft to deliver it because, in those instances, the graft is not specifically designed to self-deploy in a designated manner.

Examples are referred to herein as "self-deploying" because there is at least some resilience of the one or more flexible resilient members that biases the graft to move to the second state from the first state at least once a deployment event is initiated. In some examples, the one or more flexible resilient members allow the self-deploying graft to be stable in the first state, such that a deployment operation needs to be initiated by a user starting to move the self-deploying graft into the second state. In other examples, the one or more flexible resilient members bias the self-deploying graft towards second state, when in the first state, and the one or more flexible resilient members are prevented from deploying the graft by, for example, a filament securing two or more locations of a flexible resilient member together, thereby preventing self-deployment until the filament is severed or otherwise removed. In some examples, the one or more flexible resilient members need only be loosely held together while the self-deploying graft is in the first state (e.g., being stored or during delivery into the surgical site). During deployment, the one or more flexible resilient members are permitted (e.g., selectively, restrained, or unrestrained) to untwist and the one or more flexible resilient members (e.g., a flexible metal ring) move themselves and the graft material into the second state where the size of the graft (e.g., coverage area) is expanded. While in some examples the overall shape of the one or more flexible resilient members in the first state is generally circular, the shape of the unfurled one or more flexible resilient members may be circular, ovoid, or obround. Stated simply, there are two states: a thicker, but smaller diameter pre-deployment state and a thinner, but larger diameter post-deployment state. In both states, the implant is specifically designed to be held in that state without outside influence.

Example implementations of the overall deployment strategy described above can include several possible modifications. First, in some examples, the one or more flexible resilient members may or may not need to be removed after deployment. On one hand, the graft structure provided by the one or more flexible resilient members in the second state can facilitate holding the self-deploying graft in a desired shape and can be a secure anchoring point for sutures/anchors attaching the graft to the humerus or glenoid. Examples include self-deploying grafts configured to have the one or more flexible resilient members removed after deployment and/or attachment to tissue. To enable removal or the one or more flexible resilient members, examples include one flexible resilient member that can be cut in situ with existing arthroscopic instruments and then removed. In some examples, instead of a ring, the flexible resilient members can be linear, but with one of a variety of attachment mechanisms to temporarily hold two ends together at one or more junctions. There are wide varieties of possible junction configurations, but it can be advantageous to have arrangements that are arthroscopically separable. The flexible resilient member can be, by way of non-limiting examples, embedded in the graft material of the self-deploying path, sandwiched between two layers of graft material, or sewed into a roughly peripheral and circumferential sleeve disposed on or about a surface of the graft material. In some examples, where the flexible resilient member is to be removed, then at least one section of the flexible resilient member can be exposed to be above the surface of the patch.

Examples of flexible resilient member include specific metal alloys appropriate for the desired self-deployment function, such as nitinol, or stainless steel would be possible. In some instances, the flexible resilient member includes at least a partial shape memory so that the flexible resilient member at least partially drives the untwisting/unfolding from the first state to the second state. In some instances, the patch system includes more than two states, such that one or more intermediate or two or more post-deployment or pre-deployment states are possible. In some instances, the flexible resilient member is made from a plastic or polymer, which can include polymers with at least some shape memory.

Examples of the self-deploying patch can include a variety of different configurations in the pre-deployed state (e.g., first state), including examples that define a number of different small rings in the pre-deployed state. For some configurations, having rings (e.g., the shape of each overlapping section of the flexible resilient member) in the pre-deployed state means each ring is smaller in diameter, thus facilitating easier entry into the body. In some examples, the diameter or width of the rings can be less than about 10 mm. However, smaller rings necessarily mean that their diameter is smaller and therefore the radius of curvature is smaller, which can conflict with the material properties of the deployment wire at some point where the deployment wire will kink, which is unlikely to be fully un-kinked during a deployment. For a representative example, an overall size of a patch can be approximately 40 mm×approximately 40 mm in a deployed state (e.g., second state), and can be formed into four (4) smaller rings in the pre-deployed state, which each smaller ring being approximately in the range of about 15 mm to about 20 mm in diameter.

Another consideration is that there must be sufficient room in the surgical site (e.g., subacromial space) to fully deploy the patch. During a process of inserting a self-deploying patch (in the pre-deployed state) into a subacromial space, the compact arrangement of the flexible resilient members (e.g., wire rings), some examples can include a means for holding the patch together or constrained in some way to prevent early or uncontrolled deployment. To that end, examples can include a simple loop of suture or other severable or de-coupleable material to hold the self-deploying patch together such that once the patch is inserted into the surgical site, the loop of suture can be cut (or other materials removed or de-coupled) and the patch will self-assemble into its deployed condition.

Examples of the present disclosure include self-deploying tissue augmentation constructs that can be associated with the suture(s) in an on-demand fashion so that a surgeon can quickly and easily expand the footprint of the sutures, or similarly purposed materials such as suture tape, being used based on the needs presented during the procedure. The constructs can be associated with suture using a variety of techniques, including disposing the constructs on the suture and threading the suture through the constructs, among other techniques. In some exemplary embodiments, a tissue augmentation construct is predisposed on a threader, and the threader is operable to associate a suture being used in the soft tissue repair with the tissue augmentation construct. Surgical procedures that utilize the tissue augmentation constructs provided for in the present disclosure are also provided, as are various manufacturing techniques and methods for forming tissue augmentation constructs.

The terms "implant," "construct," "patch," and "graft" are used interchangeably herein and may refer to any flexible structure being brought from outside the body to inside the body. Representative examples include flat allograft to use in rotator cuff repair, however, non-sheet-like patches having more complex three-dimensional shapes, and non-biologic patches are also within the scope of the present disclosure.

In some embodiment the energy to change the patch from one state to another comes from an embedded deployment wire, such as from nitinol. In other examples, a different shape-memory materials can be used. One advantage of the deployment wire (e.g., flexible resilient member) is not only to provide at least a portion of the energy for deployment, but also to hold the graft in a deployed shape (e.g., the second state) to facilitate the patch being attached to the body via mechanical, chemical, energy, or other means.

The present disclosure also provides for various surgical procedures that can be performed using the implants of the nature disclosed herein. Examples of the present disclosure include surgical procedures for typical soft tissue repair case (e.g., rotator cuff repair), which can include the following steps: (i) performing shoulder arthroscopy and cuff repair and confirming the need for a patch; (ii) removing a self-deploying patch from a packaging; (iii) introducing the self-deploying patch in a pre-deployment state into a sub-acromial space of the patient via a cannula; (iv) deploying the self-deploying patch by cutting a suture clip or loop with arthroscopic scissors; (v) tacking the deployed patch against tissue with tissue staples that span the wire of the self-deploying patch; (vi) cutting the wire or a coupling connector coupling ends of the wire together; (vii) pulling a freed end of the wire to remove the wire from the patch and out of the surgical space via the cannula; and (viii) closing the patient as normal. A person skilled in the art, in view of the present disclosure, will appreciate that in at least some instance one or more of the listed steps may be omitted or modified in certain instances, and other steps can also be used in conjunction with such procedures.

In a representative embodiment, a self-deploying patch has an overall shape that is circular in the post-deployment configuration (e.g., second state). While other shapes are also anticipated, such as roughly square, roughly triangular, etc., the corners of these alternate shapes can be rounded.

In some embodiments, a self-deploying patch can be prepared in the pre-deployed state (e.g., first state) by folding in half and twisting the patch material together with an embedded flexible resilient member. In this way, the flexible resilient member (e.g., wire) of the patch can transition from being a large loop to two folded together smaller loops. This can be advantageous because the overall profile of the patch is reduced and the flexible resilient member is still able to be compressed to turn the overall circular shape of the wire loops to ovals. An alternate method of transitioning the self-deploying patch into a pre-deployed state can be to fold and twist the flexible resilient member and patch material more than once. In this way, a group of three or more smaller loops can be folded together. These pre-deployed configurations can be even smaller diameter than the two-loop embodiment, but may risk kinking the wire if the deployed patch size was sufficiently small. Also, with three or more loops folded together, the overall profile of the patch in the pre-deployment state may be less flexible and it may be harder to pass through a cannula.

In some other embodiments, the flexible resilient member is not embedded, but rather sewn or otherwise attached to one side of the patch. In this case, a pocket that the wire sits in may be one continuous pocket or comprise a series of shorter pockets that together act to hold the flexible resilient member nominally against the patch. Similarly, the flexible resilient member can be attached to the patch in other ways, such as with an adhesive, or combination of methods. Using these alternate methods for attachment can still enable the flexible resilient member to shape the patch appropriately In some embodiments, at least a small portion of a flexible resilient member can be exposed, such as a part of the flexible resilient member that contains an attachment element between two free ends of the flexible resilient member. This arrangement can facilitate cutting of the attachment element and removal of the flexible resilient member from the patch. This arrangement can also facilitate insertion of the patch into the body as this exposed area of the flexible resilient member can be used as an interface with a push rod. However, examples include a flexible resilient member fully embedded inside a patch material regardless of whether the flexible resilient member will be removed or not. In other examples, a self-deploying patch in the pre-deployment state can be rolled to facilitate passage through a cannula and subsequently unrolled in the surgical site with the assistance of the flexible resilient member because the flexible resilient member prefers to be in an un-rolled state and can, either immediately or after an initial un-rolling movement, fully or partially unroll the patch to form a post-deployment (e.g., to be installed) state.

In some embodiments, a flexible resilient member is removable from the patch following successful deployment and attachment of the patch, but an alternate embodiment can be for the wire to remain behind in the patch. An advantage to leaving the flexible resilient member behind in the patch is that the flexible resilient member can provide a more rigid point of fixation for the attachment of the patch material to tissue. For example, if the patch material had little structural strength, then the flexible resilient member can be sutured or otherwise mechanically attached directly to tissue (e.g., a rotator cuff). The flexible resilient member can be a permanent implant or, alternatively, a second operation can be used to remove the flexible resilient member, for example following healing of the soft tissue.

In some embodiments, a tissue augmentation kit can include a self-deploying patch disposed in packaging, which can be in the pre-deployed or post-deployment state. The packaging can permit sterilization of the patch with embedded flexible resilient member and shipping in the pre-deployment, or first state. In examples where the patch is desired to be in the pre-deployment state, preventing pre-deployment can be achieved by constraining the self-deploying patch radially or orthogonally, or both. Containment of the self-deploying patch can also be achieved by attaching a removable film or clip to the patch that holds the patch in place. Packaging can include, for example, a sterile bag or container that is sealer or resealable that completely contains the self-deploying patch, with or without an associated wire(s) or suture(s). Alternatively, packaging examples include the patch packaged separately from the flexible resilient member. In these examples, two sterile parts, the flexible resilient member and patch material, can be brought together on the back table of the operating room and assembled. Threading of the flexible resilient member through one or more pockets or lumens in the patch material can be conducted using a curved threader.

A variety of well-known methods could be used to deploy the patch, such as by cutting a sacrificial link between ends of a flexible resilient member or by pulling an elongate element through a thin film in a cheese-wiring action. In another embodiment, more than one patch can be deployed in a sequential or parallel effort. These techniques can either be used separately, or joined together to form a larger, single graft.

Embodiments of the self-deploying patches can include additional elongate elements, such as sutures or tapes, already attached to the patch for the user. These sutures can be used to facilitate attachment of the patch to tissue.

One example of the present disclosure is a method of soft tissue repair that includes introducing a self-deploying tissue augmentation patch to a surgical repair site, the patch being introduced in a pre-deployment state and the self-deploying patch having a flexible resilient member that is configured to assist in the deployment of the self-deploying patch from the pre-deployment state to the post-deployment state. The method further includes, after introducing the self-deploying tissue augmentation patch to the surgical site, initiating at least a deployment operation of the self-deploying tissue augmentation patch, the deployment operation moving the self-deploying tissue augmentation patch from the pre-deployment to the post-deployment state, and coupling the self-deploying tissue augmentation patch in the post-deployment state to tissue in the surgical repair site. Where the tissue augmentation patch in the post-deployment state defines a first length, a first width, and a first thickness, the tissue augmentation patch in the pre-deployment state defines a second length, a second width, and a second thickness, at least one of the second length or second width being smaller than the respective first length or first width, and the second thickness being greater than the first thickness. Additionally, in the pre-deployment state, at least a portion of the tissue augmentation patch is overlapping with a different portion of the tissue augmentation patch, and, during at least a final portion of the movement from the pre-deployment state towards the post-deployment state, the flexible resilient member urges the movement of the tissue augmentation patch towards the post-deployment state. In some examples, in the pre-deployment state, at least a portion of the flexible resilient member is overlapping with a different portion of the flexible resilient member.

The flexible resilient member can include a wire. The wire can defines a shape memory that preferentially biases the wire to move the tissue augmentation patch towards the post-deployment shape. In some examples, the flexible resilient member defines a first rounded closed curve in the post-deployment state and two or more second rounded closed curves in the pre-deployment state, the first curve having a maximum chord greater than a maximum chord of either of the two or more second rounded closed curves. The least a portion of the flexible resilient member can be embedded in the tissue augmentation patch. A different portion of the flexible resilient member can be exposed at an opening in the tissue-facing surface or the second surface. The method can include removing the flexible resilient member from the tissue augmentation patch via the opening after the self-deploying tissue augmentation patch is moved to the post-deployment state.

The movement from the pre-deployment state towards the post-deployment state can include a twisting movement and a folding movement of the tissue augmentation patch such that, in the pre-deployment state at least a portion of the tissue-facing surface is opposing a portion of the second surface.

In some examples, the method includes removing the flexible resilient member from the tissue augmentation patch in the post-deployment state. The removing action can occurs during or after coupling the self-deploying tissue augmentation patch in the post-deployment state to the tissue in the surgical repair site. Introducing the self-deploying tissue augmentation patch to the surgical repair site can include providing an insertion force to the tissue augmentation patch by urging an insertion instrument against an exposed portion of the flexible resilient member.

In some examples, the second surface of the tissue augmentation patch includes a plurality of loops or pockets through which the flexible resilient member is disposed to couple the flexible resilient member with the tissue augmentation patch. The flexible resilient member can defines a first end and a second end, the flexible resilient member further defining a closed curve such that the first is disposed adjacent to the second end, the second end and the first end being one of removably coupled or severably coupled together. The tissue augmentation patch can include a one of a severable coupling or a removable coupling securing the tissue augmentation patch in the pre-deployment state, the method further including removing or severing the coupling. In some examples, the flexible resilient member is configured to urge the tissue augmentation patch in the pre-deployment state towards the post-deployment state against the coupling such that one or severing or removing the coupling initiates movement of the tissue augmentation patch towards the post-deployment state.

In some examples, the flexible resilient member urges the tissue augmentation patch in the pre-deployment state towards the post-deployment state against the coupling such that the flexible resilient member in the pre-deployment state initiates movement of the tissue augmentation patch towards the post-deployment state.

Examples include the tissue augmentation patch include at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, or fascia. In some examples, the tissue augmentation patch includes collagen.

Another example of the present disclosure is a self-deploying soft tissue repair system, that includes a tissue augmentation patch having a first layer of material, a tissue-facing surface, and a second surface opposed to the tissue-facing surface. The system includes a flexible resilient member coupled to the tissue augmentation patch, where the tissue augmentation patch and the flexible resilient member together define a post-deployment state in which the tissue augmentation patch defines a first length, a first width, and a first thickness, and the tissue augmentation patch and the flexible resilient member together define a pre-deployment state in which the tissue augmentation patch defines a second length, a second width, and a second thickness, at least one of the second length or second width being smaller than the respective first length or width, and the second thickness being greater than the first thickness. In the pre-deployment state, at least a portion of the tissue augmentation patch is overlapping with a different portion of the tissue augmentation patch, the self-deploying soft tissue repair system is moveable between the pre-deployment state and the post-deployment state, and, during a movement from the pre-deployment state towards the post-deployment state, the flexible resilient member is configured to complete the movement of the tissue augmentation patch to the post-deployment state.

In some examples, in the pre-deployment state, at least a portion of the flexible resilient member is overlapping with a different portion of the flexible resilient member. The flexible resilient member can include a wire. The wire can define a shape memory that preferentially biases the wire to move the tissue augmentation patch towards the post-deployment shape. In some examples, the flexible resilient member defines a first rounded closed curve in the post-deployment state and two or more second rounded closed curves in the pre-deployment state, the first curve having a maximum chord greater than a maximum chord of either of the two or more second rounded closed curves.

The movement from the pre-deployment state towards the post-deployment state can include a twisting movement and a folding movement of the tissue augmentation patch such that, in the pre-deployment state at least a portion of the tissue-facing surface is opposing a portion of the second surface. The least a portion of the flexible resilient member can be embedded in the tissue augmentation patch. In some examples, a different portion of the flexible resilient member is exposed at an opening in one of the tissue-facing surface or the second surface. In some examples, the flexible resilient member is configured to be removed from the tissue augmentation patch via the opening.

The second surface of the tissue augmentation patch can include one of a plurality of loops or a plurality of pockets through which the flexible resilient member is disposed to couple the flexible resilient member with the tissue augmentation patch. In some examples, the flexible resilient member defines a first end and a second end, the flexible resilient member further defining a closed curve such that the first is disposed adjacent to the second end, the second end and the first end being one of removably coupled or severably coupled together. The system can further include one of a severable coupling or a removable coupling securing the system in the pre-deployment state. In some examples, the flexible resilient member is configured to urge the system in the pre-deployment state towards the post-deployment state against the coupling such that one of severing the coupling or removing the coupling initiates movement of the system towards the post-deployment state.

In some examples, the flexible resilient member is configured to urge the system in the pre-deployment state towards the post-deployment state against the coupling such that the flexible resilient member in the pre-deployment state initiates movement of the system towards the post-deployment state. The tissue augmentation patch can include at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, or fascia. In some examples, the tissue augmentation patch includes collagen.

The tissue augmentation patches can have a number of different configurations. In one configuration, the tissue augmentation patch includes an opening that extends through the tissue augmentation patch with the a suture limb being disposed through the opening of the first tissue augmentation block such that the tissue augmentation patches freely passes along a length of the suture limb in an unrestricted manner. In configurations where the system includes first and second tissue augmentation patches, the first and second tissue augmentation patches can have the same or different configurations. The patches can have a variety of configurations, shapes, and sizes, and can be made of a variety of materials. Further, in some embodiments, the tissue augmentation patch can include at least one of: fabric, plastic, synthetic polymer, natural polymer, collagen, collagen scaffold, reconstituted collagen, a biological autograft, allograft, allogenic, xenogeneic, or xenograft, connective tissue including human dermal matrix, acellular porcine dermal matrix, acellular bovine dermal matrix, periosteal tissue, pericardial tissue, and/or fascia, and combinations thereof. In some embodiments, the tissue augmentation patch includes collagen. The patches can be woven, non-woven, knitted, or manufactured using a variety of techniques known to those skilled in the art or otherwise provided for herein. Still further, in some embodiments, a first layer of the patch can include a biodegradable polymer, and a second layer of the patch can include an extracellular matrix. A thickness of the first layer can be greater than a thickness of the second layer.

The patch or scaffold can include a second layer of material disposed above the first layer of material such that the second layer of material is disposed above the tissue-facing surface of the scaffold and the second layer of material includes the second surface of the scaffold. In such embodiments, a suture limb can be disposed between a top-most surface of the first layer of material that is opposed to the tissue-facing surface of the patch and a tissue-facing surface of the second layer of material that is opposed to the second surface of the patch.

Unless otherwise specified, such as instances in which advantages are described related to delivering a tissue augmentation construct to a surgical repair site prior to performing the repair, the steps of the methods provided for in the present disclosure can be performed in any order.

DETAILED DESCRIPTION

Figures 1A, 1B, 1C:
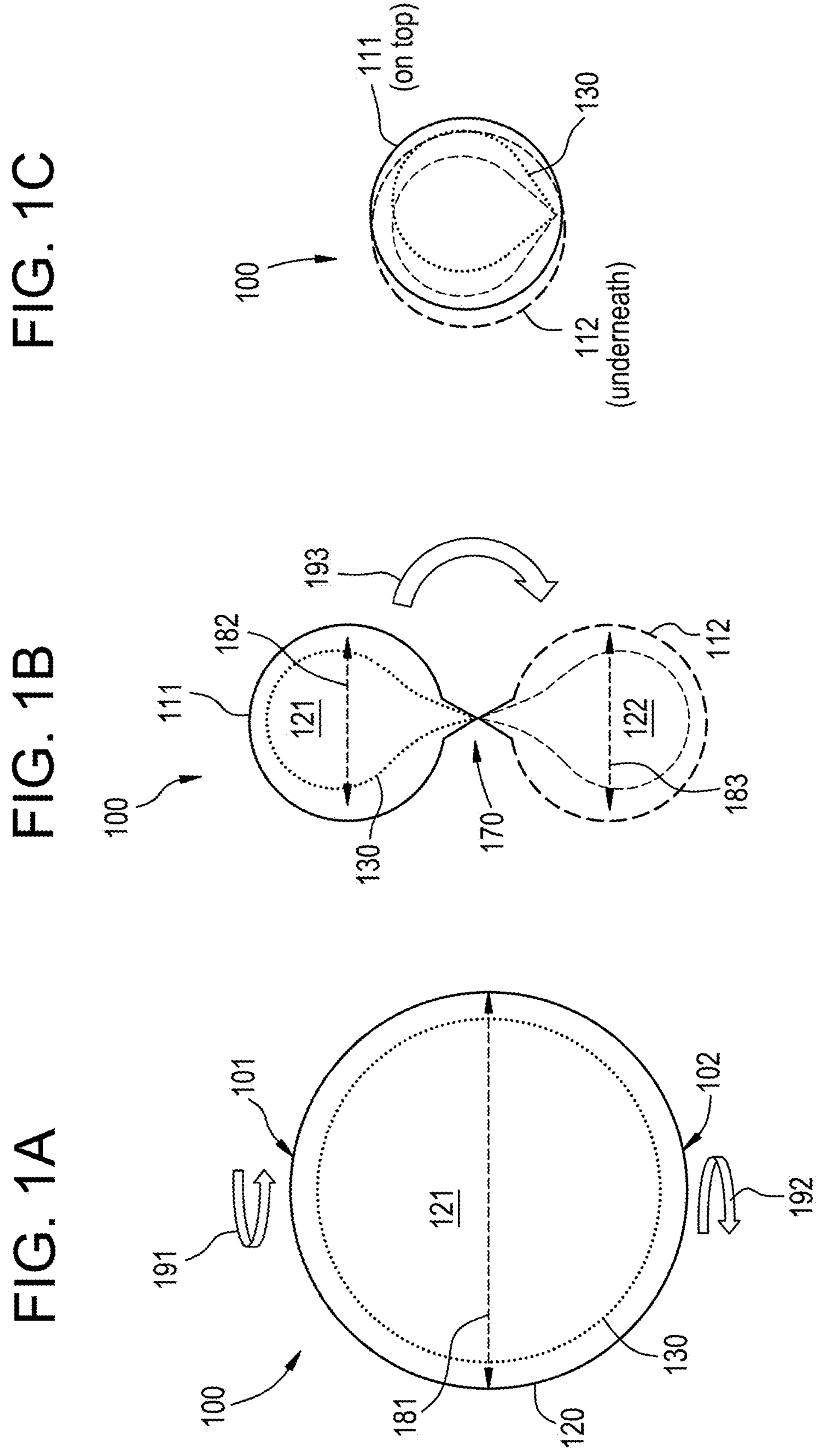
FIG. 1A is a top view of one embodiment of a self-deploying tissue augmentation construct in a deployed state.
FIG. 1B is a top view of the tissue augmentation construct of FIG. 1A during a transition from a deployed state to a compact state.
FIG. 1C is a top view of the tissue augmentation construct of FIG. 1A in a compact state.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction of movement, these arrows are illustrative and in no way limit the direction the respective component can or should be moved. A person skilled in the art will recognize other ways and directions for creating the desired result in view of the present disclosure. Additionally, a number of terms may be used throughout the disclosure interchangeably but will be understood by a person skilled in the art. By way of non-limiting example, the terms suture, filament, and flexible members may be used interchangeably, and includes other similarly purposed materials, such as suture tape. Further, the implants, constructs, grafts, and patches disclosed herein are not limited to a round shape or a rectangular shape, or any shape for that matter. Still further, to the extent the term "thread" is used to describe associating one component with another, the term is not limited to mean actually passing filament through another material. It can also include passing it through an opening (e.g., an opening formed in a body, as described below at least with respect to some tissue augmentation grafts), and thus can more generally mean associating one component with another. To the extent "features" or "step orders" are described as being a "first feature" or "first step," or a "second feature" or "second step," such ordering is generally arbitrary, unless specifically indicated otherwise, and thus such numbering can be interchangeable.

Systems, devices, and methods for soft tissue repair are generally provided, with such systems or devices including but not being limited to: one or more surgical repair filaments and/or flexible members; one or more tissue augmentation constructs or scaffolds, which include grafts, blocks, and/or patches, each of which is described in greater detail below; and one or more suture implants or similarly configured or purposed devices. The terms "tissue augmentation construct" and "tissue augmentation patch" may also be interchangeably used with the terms "augmentation construct" and "augmentation patch," and the terms "construct," "patch," and "graft." Surgical repair filaments can come in a variety of configurations including in typical suture configurations and tape forms, and can be used in connection with a variety of types of suture implants, e.g., filament anchors, suture anchors, or bone anchors, including hard and soft anchors, to attach or reattach soft tissue to bone. The repair filaments can pass through soft tissue so that the soft tissue can be positioned in a desired location. The repair filaments are secured to anchors which, in turn, are fixed in bone. The tissue augmentation construct(s) can be associated with the surgical repair filaments to increase coverage and bulk to compromised or degenerate soft tissue, to increase a surface area along which compression between the suture repair filament and tissue being repaired is applied, and to help promote tissue growth and repair. While each of the repair filament, tissue augmentation construct, and suture implant is described as being part of the systems or devices, any one component can be provided for separately for use with the other components or other implants and devices used in surgical procedures.

While many different repair procedures can be enhanced by the present disclosure, in some exemplary embodiments the soft tissue repair devices and systems provided for herein can be used for rotator cuff fixation procedures. In rotator cuff fixation procedures a surgeon can reattach the rotator cuff to the bone by first threading a suture through the soft tissue such that two suture limbs extend from the tissue. The surgeon can thread each of the suture limbs through respective tissue augmentation constructs, and subsequently fix the suture limbs to one or more bone anchors proximate to the tissue. The tissue augmentation constructs increase the surface area, or footprint, of the system that contacts the soft tissue. This enlarged footprint may disperse any loading forces on the soft tissue, and, as a result, the tensioned suture may be less likely to abrade or otherwise damage the soft tissue, for instance by "cheese wiring." Alternatively, the tissue augmentation constructs can be easily and quickly secure to tissue over a completed soft tissue repair using sutures along or using suture with another tissue augmentation patch. Still further, the tissue augmentation constructs can be made from biocompatible materials (e.g., collagen), among other types of materials, such that during healing new bands of tissue growth can occur, further increasing the efficacy of the rotator cuff fixation procedure. In other non-limiting exemplary embodiments disclosed herein, the soft tissue repair devices and systems can be used in other soft tissue repair procedures for example, repair of torn anterior cruciate ligament (ACL), instability or glenoid procedures, meniscal repair, superior capsule reconstruction, and hip capsular closure, among others. Various methods of manufacturing the tissue augmentation constructs, as well as using installation tools and/or threaders to associate tissue augmentation constructs with operative sutures are also described.

Further details regard soft tissue repair methods, suture constructs, and tissue augmentation scaffolds and patches can be found in U.S. patent application Ser. No. 16/445,930, filed Jun. 19, 2019, and entitled "TISSUE AUGMENTATION CONSTRUCTS FOR USE WITH SOFT TISSUE FIXATION REPAIR SYSTEMS AND METHODS," which is incorporated by reference herein in its entirety. The terms "patches" and "scaffolds" may be used interchangeably herein.

Self-Deploying Tissue Augmentation Constructs

FIGS. 1A-1C illustrate an example self-deploying graft 100 that has a post-deployment configuration (as shown in FIG. 1A), a pre-deployment configuration (as shown in FIG. 1C), and an ability to move between these two configurations (as shown in FIG. 1B). The self-deploying graft 100 includes a wire 130 (e.g., a deployment wire, also referred to herein as a flexible resilient member, and shown in more detail in FIGS. 2A and 2B) that is coupled with the self-deploying graft 100 such that the shape of the wire at least partially defines the shape of the self-deploying graft 100. The wire can preferentially bias the movement of the self-deploying graft 100 towards the post-deployment state such that the wire at least partially urges or drives the movement of the self-deploying graft 100 from the pre-deployment configuration to the post-deployment configuration.

As shown in FIG. 1A, the self-deploying graft 100 can have a generally circular shape and the wire 130 can have a generally circular shape, though both the self-deploying graft 100 and wire 130 can be any shape. In the illustrated embodiment, the self-deploying graft 100 has a first side 121 and a second side 122, either of which can be a tissue-facing side. In FIG. 1A, the self-deploying graft 100 is shown to have a top 101 and a bottom 102, with one or both being twisted (as indicated by respective arrows 191, 192) in opposite directions to achieve an intermediate position, as shown in FIG. 1B.

In FIG. 1B, the self-deploying graft 100 is twisted into a first portion 111 and a second portion 112, which each portion 111, 112 having a respective size (as shown by respective chords 182, 183 that are indicating a maximum width) that is less than the overall size (as shown by chord 181 in FIG. 1A) of the self-deploying graft 100 in the post-deployment configuration of FIG. 1A. Also, in FIG. 1B, while the first portion 111 of the self-deploying graft 100 maintains the first side 121 being up (e.g., the same side visible in FIG. 1A), the rotation 192 of the bottom end 102 of the self-deploying graft 100 to form the second portion 112 has disposed the opposite, second side 122 in the same orientation as the first side 121 in the first portion 111. As a final movement to reach a pre-deployment configuration (e.g., a compact arrangement), the self-deploying graft 100 can be folded (as indicated by arrow 193) about the region 170 between the first and second portions 111, 112 (e.g., a twisted region) to dispose the first portion 111 on top of the second portion 112, as shown in FIG. 1C.

From the pre-deployment configuration of the self-deploying graft 100 in FIG. 1C, the self-deploying graft 100 can be introduced to a surgical soft tissue repair site and then subsequently "deployed" by returning the self-deploying graft 100 to the configuration of FIG. 1A by going through the intermediate position of FIG. 1B. The movement from pre-deployment to post-deployment can be assisted by the material and shape properties of the wire 130, such that, for example, once the first and second portions 111, 112 are started to be separated, the wire 130 urges the self-deploying graft 100 to partially or completely (e.g., without additional assistance) return to the post-deployment configuration, which represents a stable position (e.g., small movements of the self-deploying graft 100 away from the post-deployment configuration will result in the wire 130 urging the self-deploying graft 100 back to the post-deployment shape). In some instances, the self-deploying graft 100 is stable in both the pre-deployment configuration and the post-deployment configuration such that an initial movement of the self-deploying graft 100 away from the pre-deployment configuration is needed before the wire 130 will return the self-deploying graft 100 to the post-deployment configuration without additional assistance. In other instances, the self-deploying graft 100 is not stable in the pre-deployment configuration and is instead held in this configuration before, during, and/or after introduction to a surgical repair site by a removeable or severable coupling (e.g., a tape or suture) that prevents the first portion 111 from moving away from the second portion 112. In such a configuration, the self-deploying graft 100 "springs" into the post-deployment configuration once freed from the coupling.

Figure 2B:
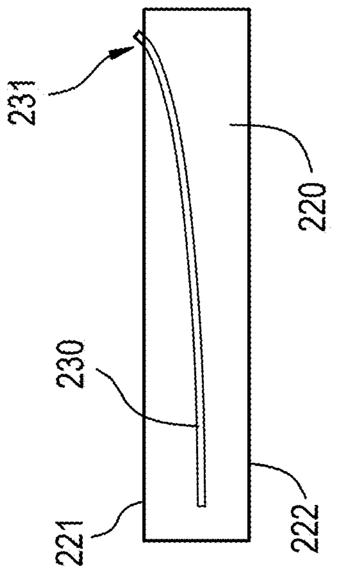
FIG. 2B is a side view of the self-deploying tissue augmentation construct of FIG. 2A.
Figure 2A:
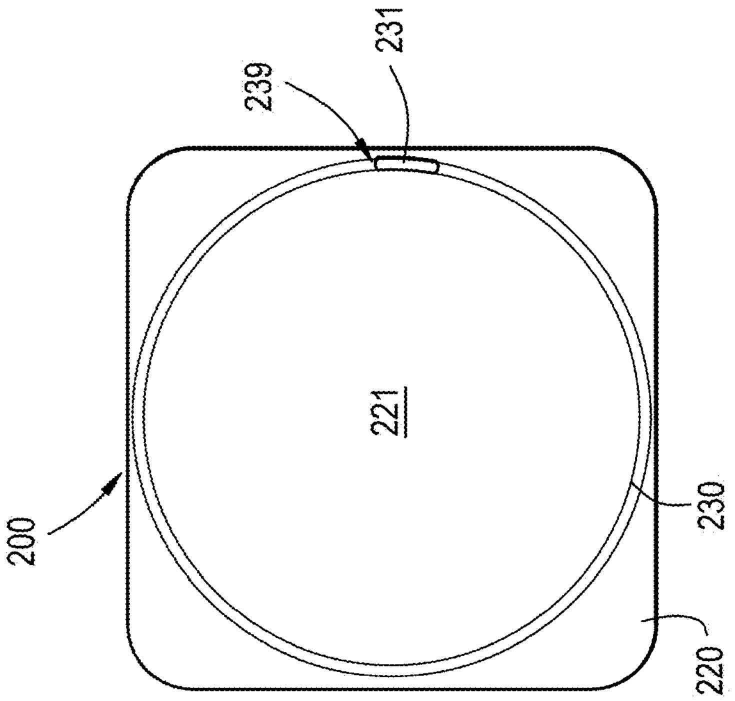
FIG. 2A is top view of another embodiment of a self-deploying tissue augmentation construct having a flexible resilient member disposed therein.

Additional details about wires of the nature of the wire 130 are shown in FIGS. 2A and 2B, which are top and side views, respectively, of another embodiment of a self-deploying graft 200 having a wire 230 disposed in material 220 that forms the graft 220. The self-deploying graft 200 has a generally rectangular shape and the wire 230 has a generally circular shape. The wire 230 is almost completely contained within the material 220 of the self-deploying graft 200 (as shown more clearly in FIG. 2B), with a portion 231 of the wire 230 exposed though an opening 239 in a first surface 221 of the material 220 of the self-deploying graft 200. The opening 239 can be, for example, pre-formed in the material 220, either with an instrument or as part of the material's construction, or the opening 239 can be created pre-deployment to enable insertion of the wire 230 before In some examples, the wire 230 can be severed or otherwise separated at the exposed portion 231 such that the wire can be removed from the material 220 via the opening. In operation, for example, the self-deploying graft 200 can be introduced to a surgical repair site in a pre-deployment configuration and subsequently deployed into the post-deployment configuration shown in FIGS. 2A and 2B. Next, an arthroscopically-separable junction that is exposed at portion 231 above the first surface 221 of the material 220 can be separated and the wire 230 can be drawn out of the material 220 before closing access to the surgical site and before, after, or during the repair operation, in which a tissue-facing side 222 of the self-deploying graft 200 can be positioned against tissue being repaired. Additionally, the exposed portion 230 can provide a convenient landing for applying a force to the self-deploying graft 200, such as to push the self-deploying graft 200 though a cannula and into a surgical repair site, as shown in more detail in FIGS. 3A and 3B.

Figure 3B:
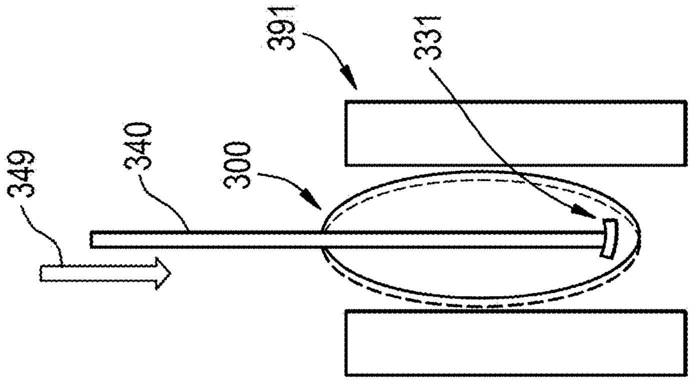
FIG. 3B is a schematic side view of the self-deploying tissue augmentation construct and the surgical cannula of FIG. 3A, with the construct being delivered through the cannula with an insertion tool.
Figure 3A:
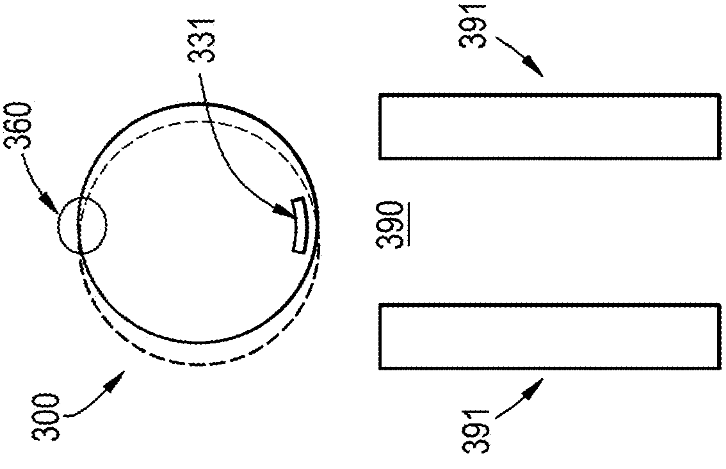
FIG. 3A is a schematic side view of a self-deploying tissue augmentation construct in a compressed state before insertion into a surgical cannula.

In FIG. 3A, a self-deploying graft 300 is illustrated in a pre-deployment configuration (e.g., similar to that of the graft 100 of FIG. 1C), with an exposed region 331 of an internal deployment wire. The self-deploying graft 300 can be situated at an entrance 390 to a cannula 391, which can be, for example, an entrance to a surgical repair site inside a patient's body. FIG. 3B shows the self-deploying graft 300 being inserted into the cannula 391 by an insertion tool 340. The insertion tool 340 can contact the exposed region 331 of the internal deployment wire and apply a force (as indicated by arrow 349) to urge the self-deploying graft 300 into the cannula 391. As shown in FIG. 3A, the self-deploying graft 300 can include a severable or removable fixation or coupling 360 that can prevent the self-deploying graft 300 from moving out of the pre-deployment configuration. In some instances of operation, the coupling 360 can be removed prior to insertion of the self-deploying graft 300 into the cannula 391, instead, optionally, the cannula 391 can be responsible for preventing deployment of the self-deploying graft 300, while in other instances of operation the coupling 360 can be removed once the self-deploying graft 300 has passed through the cannula 391 and is in disposed proximate to or at the surgical repair site. The coupling 360 may be needed to prevent deployment of the self-deploying graft 300 in examples where the deployment wire is configured to initiate movement of the self-deploying graft 300 into a post-deployment configuration from the pre-deployment configuration, or just generally as a redundancy to prevent accidental deployment for examples where the deployment wire is configured to assist or complete deployment once the self-deploying graft 300 is disposed away from the pre-deployment configuration towards the post-deployment configuration. Once the self-deploying graft 300 has passed through the cannula 391, the graft 300 can be secured to tissue, as shown in FIG. 4.

Figure 4:
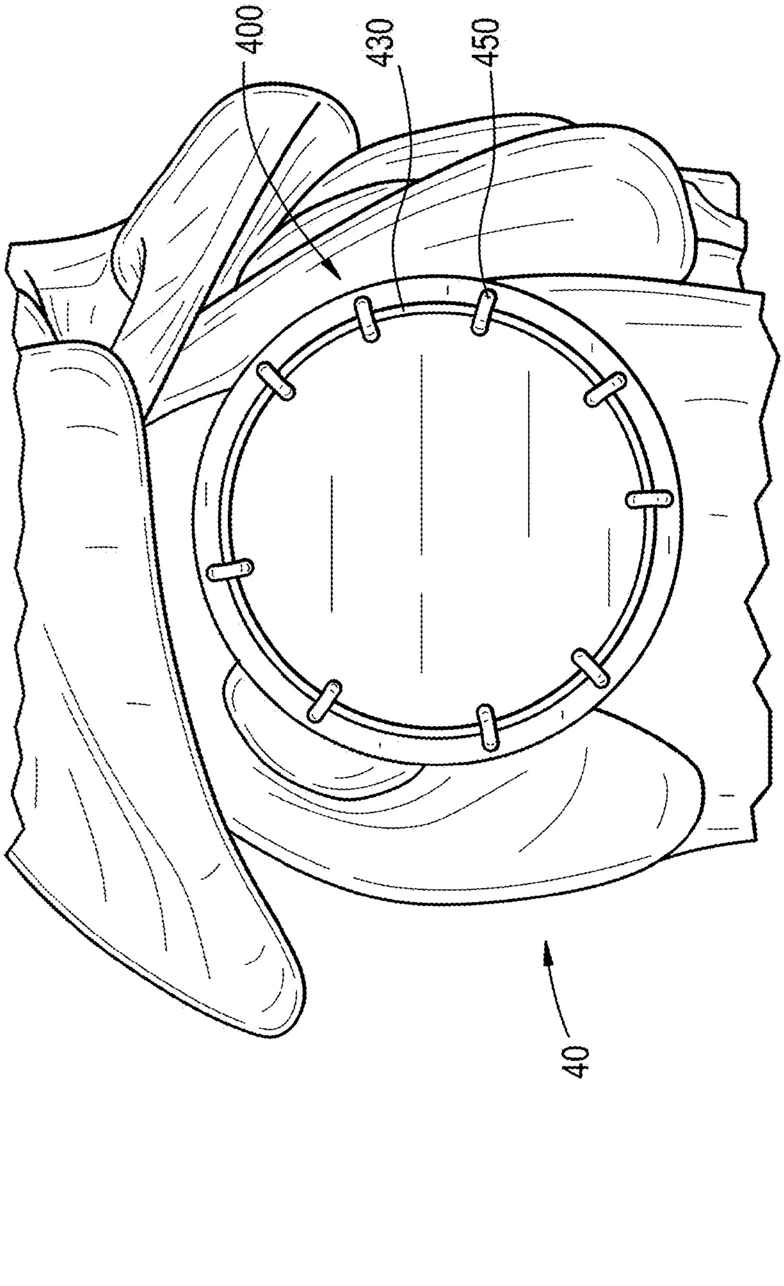
FIG. 4 is a top view of still another embodiment of a tissue augmentation construct in an installed configuration at a surgical site.

FIG. 4 is a top view of a self-deploying graft 400 in a post-deployment configuration and installed against tissue 40 (e.g., a superficial surface of rotator cuff, as shown) at a surgical repair site. The self-deploying graft 400 includes a wire 430 disposed in the material of the self-deploying graft 400. A plurality of tissue staples 450 can be used to secure the self-deploying graft 400 to the tissue 40, and, as shown, the tissue staples 450 can span across the wire 430. In some instances, the wire 430 is left in the self-deploying graft 400 to strengthen the attachment of the self-deploying graft 400 to the tissue 40. In other instances, the wire 430 can be removed after the tissue staples 450 are inserted. In some instances, one or more sutures can be used to couple the self-deploying graft 400 to the tissue 40. A person skilled in the art will appreciate other components and techniques that can be used in lieu of or in addition to staples and/or sutures for purposes of coupling the graft 400 to the tissue 40.

Figure 5A:
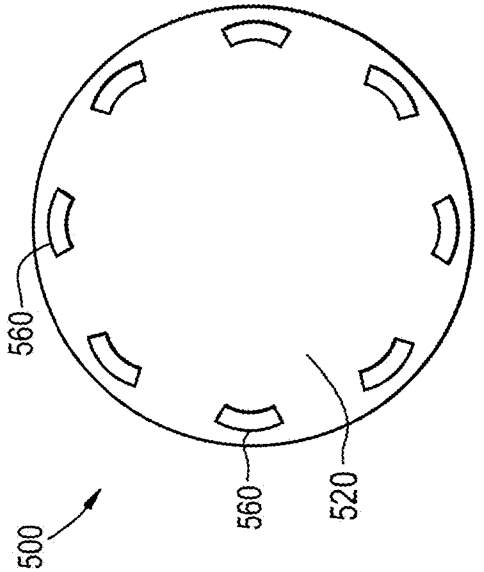
FIGS. 5A-5E are schematic sequential top views of an embodiment for installing a flexible resilient member in a self-deploying tissue augmentation construct.
Figure 5B:
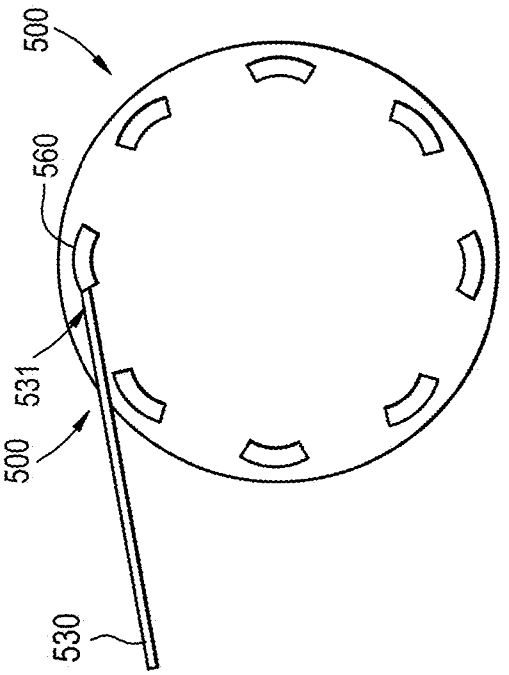
Figure 5C:
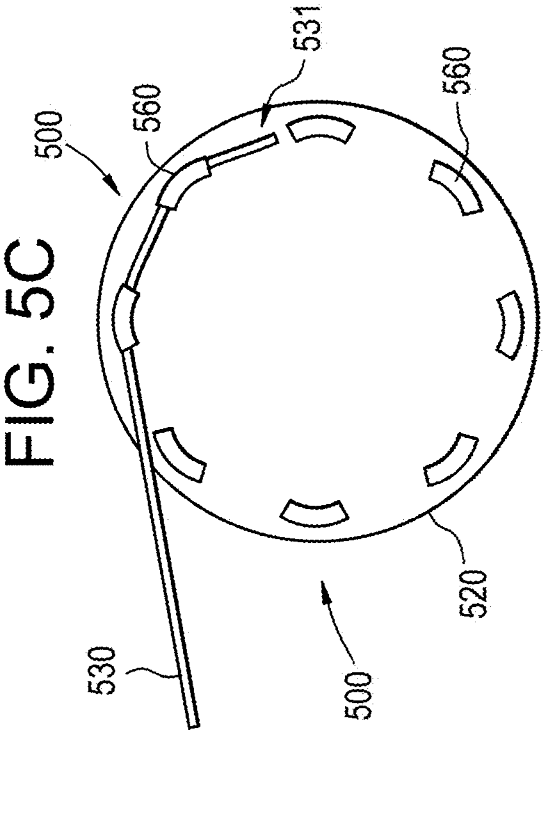
Figure 5D:
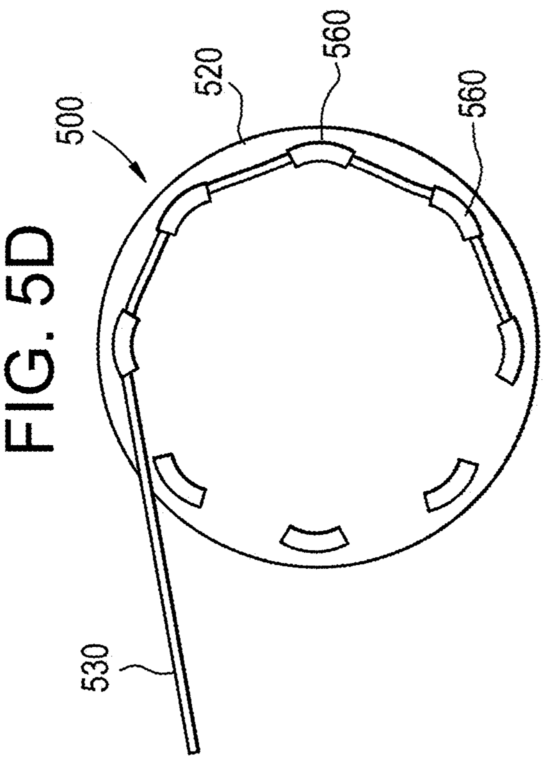
Figure 5E:
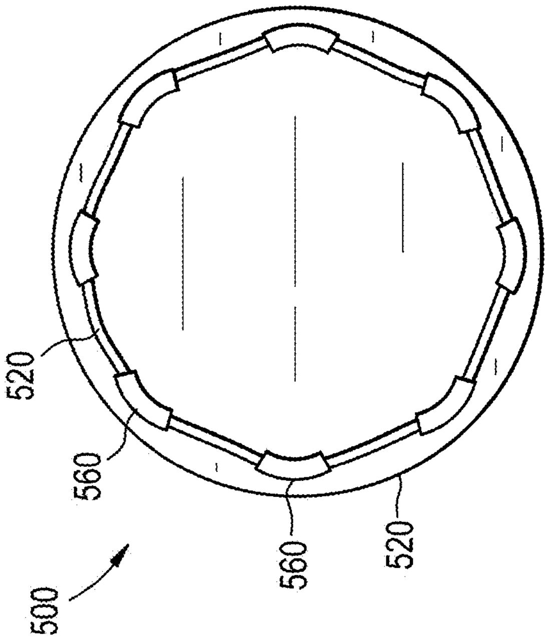

FIGS. 5A-5E are schematic sequential top views of an embodiment for installing a wire in a self-deploying graft 500. The self-deploying graft 500 can include a plurality of graft pockets 560, which can also be sutures or any other structure for coupling a wire to a material 520 of the self-deploying graft 500. In the illustrated embodiment, there are eight (8) pockets, although fewer or greater than eight are possible. The self-deploying graft 500 is shown in a post-deployment configuration and the insertion of the wire 530 can be done as part of a pre-operative preparation of the self-deploying graft 500 or as a step in the construction prior to delivery to the surgical site. FIG. 5B shows a flexible needle 531 that can be used to load the wire 530 through successive pockets 560, with increasing progress shown in FIGS. 5C and 5D, until, as shown in FIG. 5E, the wire 530 is fully threaded though the self-deploying graft 500. The ends of the wire can be coupled together using a variety of techniques provided or herein or otherwise known to those skilled in the art. Some non-limiting examples of the same are shown in more detail in FIGS. 6B-6G. Alternatively, the wire 530 can be threaded though the pockets 560 directly without the use of a tool, such as needle 531.

Figure 6D:
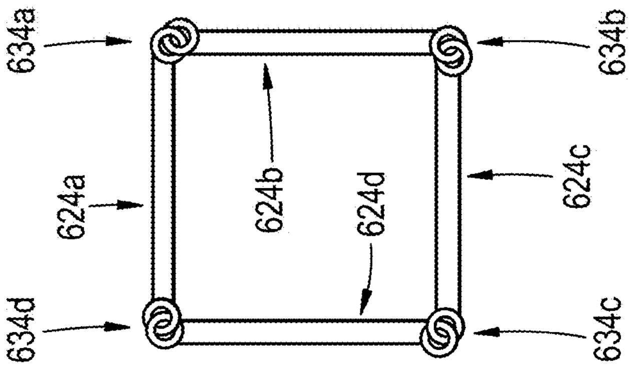
FIG. 6D is a top view of another embodiment of four severable resilient flexible members arranged for use in a self-deploying tissue augmentation construct.
Figure 6C:
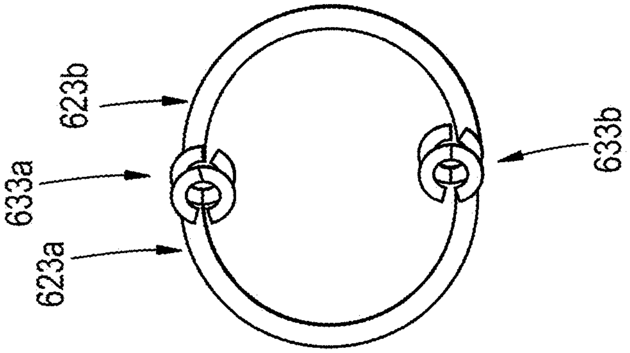
FIG. 6C is a top view of an embodiment of two severable resilient flexible members arranged for use in a self-deploying tissue augmentation construct.
Figure 6B:
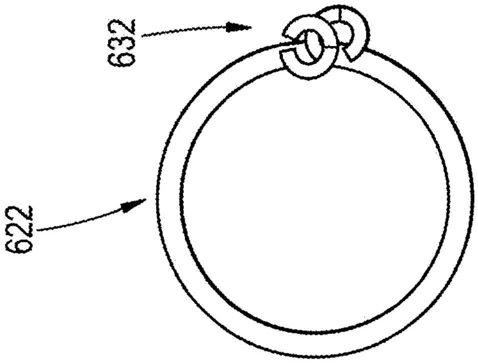
FIG. 6B is a top view of an embodiment of a severable resilient flexible member for use in a self-deploying tissue augmentation construct.
Figure 6A:
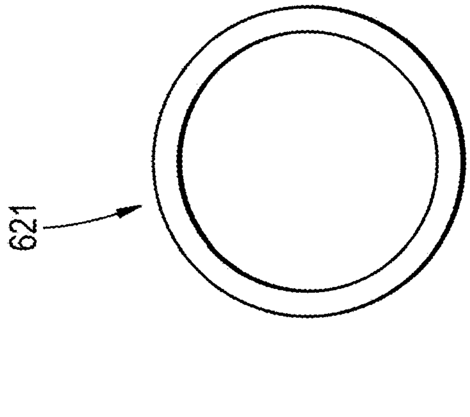
FIG. 6A is a top view of an embodiment of a resilient flexible member for use in a self-deploying tissue augmentation construct.

FIGS. 6A-6D show different configurations of a wire or wires that can be used with examples of the self-deploying grafts disclosed herein. FIG. 6A shows a continuous wire 621 with a closed circular shape that can be fully or partially embedded in the material of a self-deploying graft. The continuous wire 621 can be cut to facilitate removal from a self-deploying graft, if desired. Alternatively, a single wire segment 622 can be formed into a closed shape, as shown in FIG. 6B, with the two ends of the wire segment 622 being coupled together at a location 632 to form a closed loop. The single wire segment 622 can be fully or partially embedded in the material of a self-deploying graft and, advantageously, the location 632 can be exposed above a surface of the self-deploying graft to enable separation of the ends of the wire segment 622 by severing the coupling at the location 632. A number of different coupling techniques can be used to join the ends of the wire segment 622, a representative few of which are shown in more detail below in FIGS. 6E-6G.

FIG. 6C shows that more than one wire segment can be used to form a closed loop. In FIG. 6C, a first wire segment 623*a* is joined with a second wire segment 623*b* at two separate locations 633*a*, 633*b*. While FIGS. 6A-6C show the wire(s) forming a closed curved shape, other shapes are possible, such as a rectangular shape shown in FIG. 6D, where four linear wire segments 624*a*-624*d* are joined at 4 sequential locations 634*a*-634*d* to form a straight-sided shape. In practice, the shape of the wire(s), the coupling location(s), and/or the material of the graft itself can all contribute to a resultant shape of the wire(s) in a self-deploying graft in both a pre-deployment configuration and a post-deployment configuration.

Figure 6E:
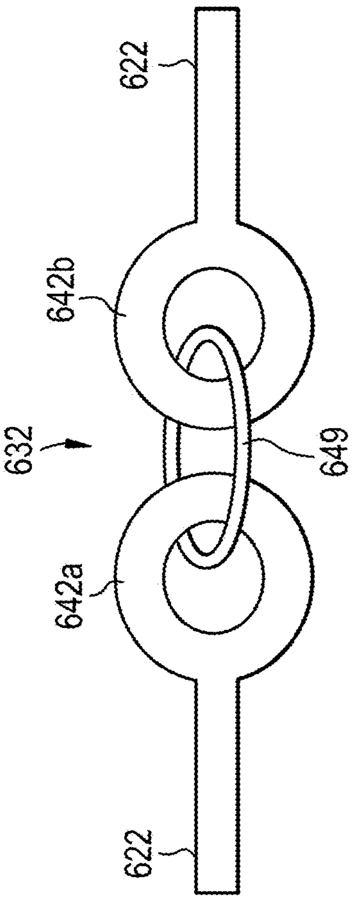
FIG. 6E is a perspective detail view of a coupling arrangement between ends of the resilient flexible member of FIG. 6B.
Figure 6F:
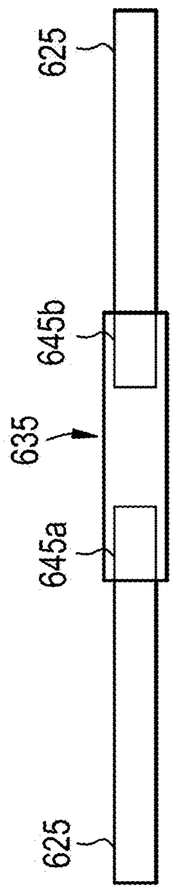
FIG. 6F is a schematic view of another coupling arrangement between ends of a flexible resilient member for use in self-deploying tissue augmentation constructs.
Figure 6G:
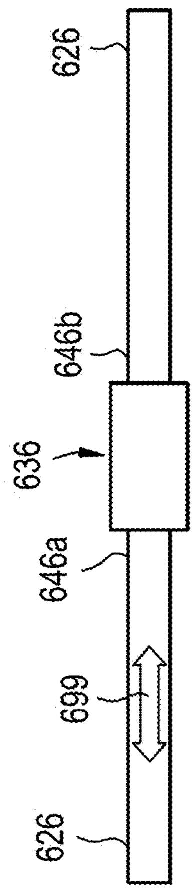
FIG. 6G is a schematic view of still another coupling arrangement between ends of a flexible resilient member for use in self-deploying tissue augmentation constructs

FIG. 6E-6G illustrate different techniques for forming a coupling (e.g., junction) between wire segments. FIG. 6E shows the ends 642*a*, 642*b* of the wire segment 622 of FIG. 6B joined together by an arthroscopically cut-able suture 649 to form a coupling 632. FIG. 6F shows ends 645*a*, 645*b* of another wire segment 625, which can be ends of separate segments, connected by an arthroscopically cut-able tape 635. FIG. 6G shows ends 646*a*, 646*b* of still another wire segment 626, which can also be ends of separate segments, connected by a slip-fitting disposed over one or both ends 646*a*, 646*b*, in turn facilitating connection or removal of the segment(s) by movement of one or both ends 646*a*, 646*b* about a longitudinal direction (as indicated by arrow 699).

Figure 7B:
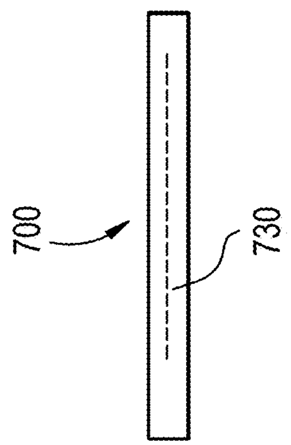
FIG. 7B is a side view of the self-deploying tissue augmentation construct of FIG. 7A in an expanded state.
Figure 7A:
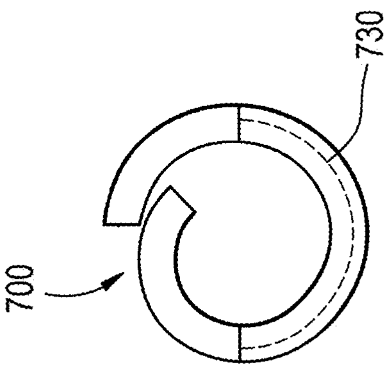
FIG. 7A is a side of another embodiment of a self-deploying tissue augmentation construct in a compressed state.

FIGS. 7A and 7B show another configuration of a self-deploying graft 700, in which the graft 700 is rolled in the pre-deployment configuration and unrolled in the post-deployment configuration. The self-deploying graft 700 includes a deployment wire 730 that biases the self-deploying graft in the post-deployment (e.g., unrolled) configuration of FIG. 7B. This configuration is distinct from, for example, patches that are rolled or otherwise folded for insertion that subsequently self-expand in some manner towards their pre-rolled or pre-folded configuration in that, examples of the present disclosure include a biasing wire or other resilient material separate from the patch material that applies a restoring force to the patch material to urge it into a post-deployment shape.

While the examples illustrated herein include wires disposed within a graft material, examples can also include one or more tunnels formed in graft material to contain one or more deployment wires. Additionally, examples include one or more of layers of, or associated with, the graft material, in which a specific pattern is created on an internal layer to facilitate a process of embedding an internal deployment wire. While the examples illustrated herein include one or more connected deployment wires that form a closed curve or loop, in some examples the curve is not closed (e.g., a partial loop). While the examples illustrated herein include a single self-deploying patch, two or more self-deploying patches can be used in a single repair, including utilizing the self-deployment wires for coupling two or more patches together, including the use of intervening suture or other elements in between the wires on different patches. In some instances a single self-deployment wire can be operated to deploy multiple self-deploying patches, while in other instances each self-deploying patch can be actuated by its own self-deployment wire. Still further, in instances in which multiple self-deployment wires are operated to deploy multiple self-deploying patches, there can be a primary self-deployment wire, which may or may not be associated with its own self-deploying patch, which can be operated to subsequently cause multiple self-deployment wires to actuate multiple self-deploying patches.

A person skilled in the art will recognize that the size and dimensions of the length, width (or diameter), and thickness of the self-deploying grafts disclosed herein can depend on a variety of factors, including but not limited to the size and shape of the wire, the size and shape of the pre-deployment configuration, the size of the filament with which it is to be associated, the anatomy of the patient, and the type of procedure being performed. A person skilled in the art will recognize that the ratio of the width or diameter of a self-deploying graft to diameter of the wire and/or diameter of the filament or related structure with which the graft is used can be any suitable ratio, depending, at least in part, on the type of filament or related structure being used, the type of strip or other construct being used, and/or the type of procedure being performed, among other factors, and thus a ratio of width to diameter may be smaller or larger than those provided for and illustrated herein. Further, in some embodiments, the self-deploying graft can be substantially flat and approximately uniform in the post-deployment configuration. In other embodiments, the self-deploying graft can have a curve or otherwise non-planar shape in the post-deployment configuration. While in some embodiments the self-deploying graft has a substantially uniform thickness, in other embodiments the self-deploying graft can have a variable thickness, including, for example, having a flat side and a curved side. A variety of other sizes and shapes of the self-deploying tissue augmentation graft, including ratios of the dimensions of the graft material and associated components (e.g., wire) can be utilized without departing from the spirit of the present disclosure.

A number of techniques can be used to associate a self-deploying graft with suture limbs. For example, a suture limb can be threaded across a top face of the graft, from a top side to a bottom side and back to the top side. Additionally, a suture limb can be threaded though the graft and the process of threading a suture limb through the material can be repeated as many times as desired. In some embodiments a suture threader can be threaded through the self-deploying graft ahead of a procedure so that the operative suture can be threaded through the graft in vivo during the procedure. Exemplary suture threaders are discussed below.

The suture limbs used in conjunction with the self-deploying graft can be any type of suture (e.g., braided filament, cannulated filament, mono filament, suture tape, etc.) and can have a size between about a #5 filament (about 20 gauge to about 21 gauge) and about a #3-0 filament (about 29 gauge to about 32 gauge). A person skilled in the art will recognize a variety of other filament types and sizes that can also be used in conjunction with the graft.

Methods of Use—Soft Tissue Repairs

Non-limiting exemplary methods for using systems, devices, and kits of the type described herein are now described in greater detail. While the methods described herein generally relate to attaching soft tissue to bone, and in this section of the disclosure are primarily discussed with respect to rotator cuff repairs, a person skilled in the art will recognize other types of procedures and repairs with which the constructs and the methods related to the same can be used. Further, to the extent a particular type of self-deploying tissue augmentation construct is illustrated in the present embodiments, a person skilled in the art would understand how to employ other self-deploying tissue augmentation constructs provided for herein, or otherwise derivable from the present disclosure, without departing from the spirit of the present disclosure. Likewise, any sutures or anchors provided for herein or otherwise known to those having skill in the art can be used, including knotless anchors. Still further, to the extent the techniques described herein discuss having a certain number of suture limbs (e.g., one, two, three, etc.) extending from or otherwise associated with a suture anchor to perform the tissue repair, a person skilled in the art, in view of the present disclosure, will understand how a different number of limbs can be used to perform the same, or a similar type, of repair. A benefit that results from each of the methods described herein is that the tissue augmentation constructs can be associated with the suture being used in the repair in an on-demand manner, thus allowing a surgeon to quickly and easily associate one or more tissue augmentation constructs with the repair suture (s) to form desired footprints for the repair. Such use can be enhanced by the self-deploying nature of the provided constructs.

The present disclosure contemplates that the self-deploying tissue augmentation constructs provided for herein have applications outside of rotator cuff repairs as augmentation constructs. Some, non-limiting examples of those procedures are provided herein. These examples are by no means exhaustive. Further, a person having skill in the art will understand how some of the disclosure provided herein can be adapted for use in rotator cuff repair procedures. Each of the embodiments described herein, including non-rotator cuff repairs (i.e., labrum repair or augmentation, ACL reconstruction, Achilles repair, AC joint-repair, meniscal repair, and superior capsule reconstruction), are conceived with respect to using a self-deploying tissue augmentation construct, which includes any of the self-deploying patches disclosed herein or otherwise derivable from the present disclosure. A person skilled in the art, in view of the present disclosure, will understand how to adapt various self-deploying tissue augmentation constructs for use in the various procedures. Further, in embodiments of each of the methods described in the present disclosure, collagen, for example, can be used as part of, or to form entirely or almost entirely, the self-deploying construct. This allows the self-deploying construct to grow in the area of the repair once healed. Other materials can also be used to form the self-deploying constructs, including others that achieve a similar result as collagen.

Figure 8:
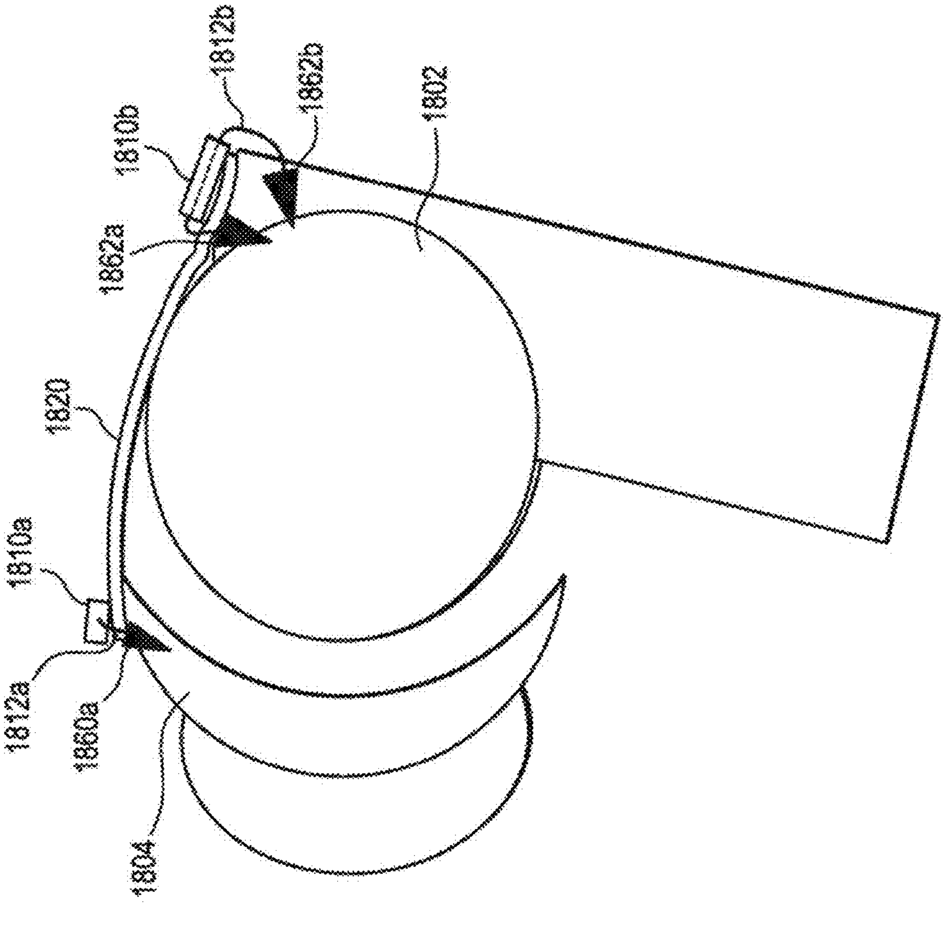
FIG. 8 is a schematic side view of another embodiment of a tissue augmentation construct, the construct being used in conjunction with a superior capsule reconstruction procedure.

A representative superior capsule reconstruction procedure is illustrated in FIG. 8. The method can optionally use at least one of additional tissue augmentation blocks 1810*a*, 1810*b* to assist in anchoring down a self-deploying superior capsule reconstruction graft 1820 over a humeral head 1802. Once the surgeon has access to the surgical site and the tissue, bone, tissue augmentation constructs, and self-deploying superior capsule reconstruction graft have been prepared according to accepted surgical techniques, including those provided for herein, the surgeon deliver the self-deploying patch to the surgical site in a pre-deployment configuration and, once able, can allow or cause the self-deploying patch to be move to the post-deployment configuration. This can include, for example, initiating a movement of the self-deploying patch and/or de-coupling a holding suture or coupler that is holding the self-deploying patch in the pre-deployment configuration. Thereafter, the surgeon can affix one end of the self-deploying graft 1820 to the glenoid rim 1804. The surgeon can affix one end of the self-deploying graft 1820 to the glenoid rim 1804 by installing a first medial anchor 1860*a* having a suture 1812*a* extending therefrom. A first tissue augmentation construct 1810*a* can be thread onto the suture 1812*a* using techniques provided for throughout the present disclosure, and the construct 1810*a* can be tightened against the self-deploying graft 1820 using techniques provided for herein or otherwise known to those skilled in the art, such as for example, by tying suture 1812*a* to suture 1812*b*, not shown, both of which extend from the anchor 1860*a*. The pressure of the construct 1810*a* on the self-deploying graft 1820 can hold the self-deploying graft 1820 at a desired location with respect to the glenoid rim 1804. An opposite end of the self-deploying graft 1820 can be anchored proximate to the humeral head 1802 and a location and/or size of the graft 1820 adjusted so that the glenoid rim 1804 is brought into contact with the humeral head 1802 in accordance with techniques used in superior capsule reconstruction procedures.

While a number of different techniques can be used to couple the other end of the self-deploying graft 1820 proximate to the humeral head 1802, in the illustrated embodiment first and second lateral anchors 1862*a*, 1862*b* are used in conjunction with a second tissue augmentation construct 1810*b* to make the repair. More particularly, in one embodiment, at least one of the anchors 1862*a*, 1862*b* can have a suture 1812*b* associated therewith and the second tissue augmentation construct 1810*b* can be disposed on at least a portion of the suture 1812*b* using techniques provided for in the present disclosure. The suture 1812*b* can extend between the two anchors 1862*a*, 1862*b*, against using any of the techniques provided for herein or otherwise known to those skilled in the art, and the construct 1810*b* can be tightened down against the self-deploying graft 1820 to help maintain a location of the self-deploying graft 1820 with respect to the humeral head 1802 while allowing the construct 1810*b* to better distribute any force applied by the suture 1812*b* across the surface area of the construct 1810*b*. Any number of tissue augmentation constructs can be used in the repair, and in alternative embodiments tissue augmentation constructs may only be used in conjunction with coupling the self-deploying graft 1820 with only one of the glenoid rim 1804 and the humeral head 1802.

Self-Deploying Tissue Augmentation Constructs—Construction Examples

Self-deploying tissue augmentation constructs can form of a patch or graft that can be associated with one or more limbs of suture to increase a footprint of the one or more limbs and to provide additional surface area across which forces to be distributed, among other benefits articulated throughout the present disclosure, e.g., enhancing healing of otherwise compromised tissue and/or providing bulk to otherwise compromised or degenerate tissue and/or tendon. The patches can be disposed on, or even attached or coupled to, the suture rather than just sitting on top of operative sutures. Further, the instant patches can be delivered to the surgical site and threaded onto sutures using a suture threader, either before or after deployment, as described herein, thereby obviating the need for extensive suturing of each edge of a patch. A number of different techniques can be used to associate the illustrated patches with suture, including threading the suture through the patch and/or disposing the suture in between layers of a scaffold or patch. The self-deploying patch can then be disposed proximate to a surgical site as described. Methods of manufacturing a scaffold or patch, and methods of installing various scaffolds and patches, are also provided for below. The systems and methods disclosed herein allow for quick, easy, and affordable techniques for preventing damage to tissue by tensioned suture.

Figure 9A:
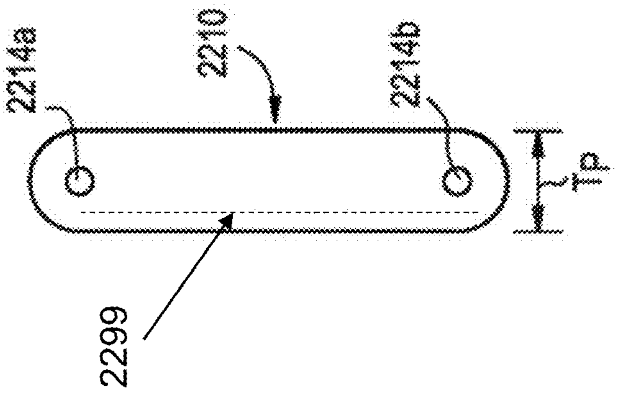
FIG. 9A is a side view of another embodiment of a self-deploying tissue augmentation construct.
Figure 9B:
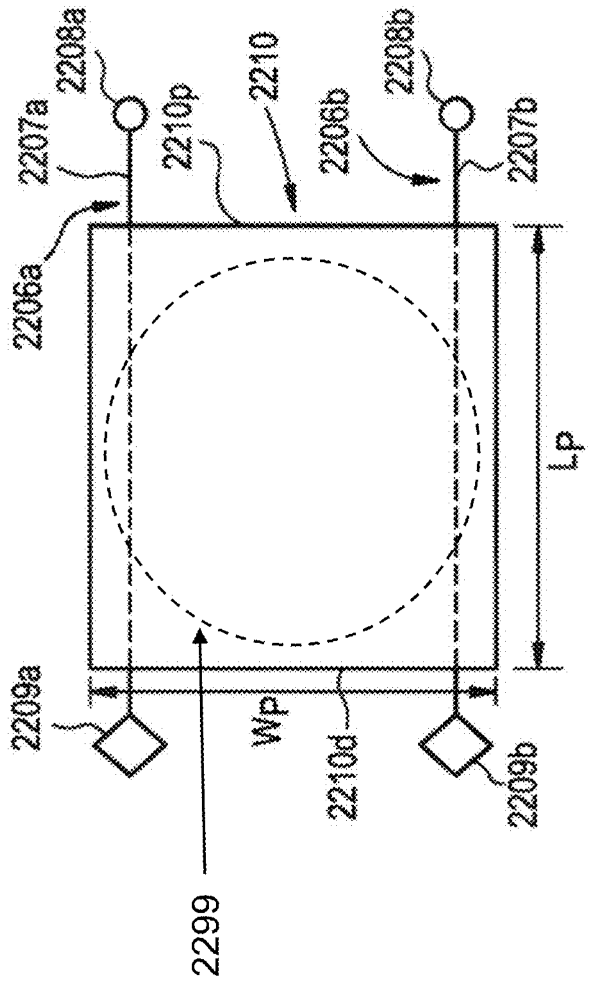
FIG. 9B is a top view of the self-deploying tissue augmentation construct of FIG. 9A, the construct having a plurality of threaders disposed therein.

One embodiment of a tissue augmentation construct 2210 having a patch or scaffold configuration is provided for in FIGS. 9A and 9B. As shown, self-deploying the tissue augmentation patch 2210 has a rectangular-shaped body and can be disposed on or otherwise associated with suture limbs 2212*a*, 2212*b* (as shown in FIGS. 9D-9F). In the illustrated embodiment the self-deploying patch 2210 is in a deployed arrangement and includes a wire 2299 (e.g., an internal wire, as shown, but could also be an external or partially internal wire) and bores or lumens 2214*a*, 2214*b* can be formed in the body and can extend therethrough from a proximal-most end 2210*p* to a distal-most end 2210*d*. Deployment of the patch can include any and all of the methods and techniques disclosed herein, including deliver the self-deploying patch to the surgical site in a pre-deployment configuration and, once able, allowing or causing the self-deploying patch to be move to the post-deployment configuration. This can include, for example, initiating a movement of the self-deploying patch and/or de-coupling a holding suture or coupler that is holding the self-deploying patch in the pre-deployment configuration. The bores 2214*a*, 2214*b* can be used, for example, to receive the suture limbs 2212*a*, 2212*b* so that the patch 2210 and limbs 2212*a*, 2212*b* can be associated with each other. As shown in FIG. 9B, the self-deploying patch 2210 can be pre-threaded with suture threaders 2206*a*, 2206*b*. The self-deploying patch of this configuration, or any configuration provided for herein, can be disposed in packaging while in a pre-deployment, post-deployment, or any other configuration before removal from the packaging. The threaders 2206*a*, 2206*b* can be configured in manners otherwise known to those skilled in the art and/or derivable from the present disclosure. The threader can include a proximal handle portion, an intermediate elongate portion, and a distal suture-receiving end. The proximal handle portion can be configured to be easily gripped by a user, for instance by having a substantially rectangular shape as shown. Other shapes and features for gripping can be provided. The intermediate portion can be a filament portion capable of having a tissue augmentation construct, e.g., self-deploying the tissue augmentation patch 2210, associated therewith, thereby allowing the threader to be flexible. Once the self-deploying the tissue augmentation patch 2210 is disposed on or is otherwise associated with the suture limb, the suture limb can be disassociated with the opening and the threader can be discarded or reused since it is no longer associated with either the augmentation patch or the suture limb. As shown, the self-deploying patch 2210 has a length $L_P$ that is substantially equal to a width $W_P$, and it also has a thickness $T_P$. Further, the thickness $T_P$ can be greater than a diameter of a filament or suture with which the tissue augmentation patch 2210 is associated, e.g., the suture limb 2212*a*.

A person skilled in the art will recognize that the dimensions of the length $L_P$, the width $W_P$, and the thickness $T_P$ of the self-deploying tissue augmentation patch 2210, as well as a diameter of the bores 2214*a*, 2214*b*, can depend on a variety of factors, including but not limited to the size of the filament with which it is to be associated, the anatomy of the patient, and the type of procedure being performed. Some exemplary, non-limiting dimensions for a tissue augmentation patch 2210 can be useful in understanding the present disclosure.

In some embodiments, the length $L_P$ can cover a significant portion, to almost an entire portion, of a length of tissue extending between a stitch made in tissue and a bone anchor used to help secure the tissue. In some embodiments, the length $L_P$ and width $W_P$ can be approximately in the range of about 10 millimeters to about 50 millimeters, and the thickness $T_P$ can be approximately in the range of about 0.5 millimeters to about 5 millimeters. The size of the diameter of the bores 2214*a*, 2214*b* can also depend on a variety of factors, including but not limited to the size of the limb to be passed therethrough. In some embodiments, the diameter can be approximately in the range of about 0.5 millimeters to about 3 millimeters.

A number of techniques known to those skilled in the art can be used to associate the self-deploying patch 2210 with the suture limbs 2212*a*, 2212*b*. Suture limbs 2212*a*, 2212*b* can be threaded or passed from the proximal-most end 2210*p* to the distal-most end 2210*d* of the patch 2210 without passing across the body of the self-deploying patch 2210, i.e., without passing through sidewalls that define the bores 2214*a*, 2214*b*. As a result, the patch 2210 can freely pass along a length of the limbs 2212*a*, 2212*b* unhindered or unrestricted. In other embodiments, the limbs 2212*a*, 2212*b* can pass across the body once or more, to further secure a location of the self-deploying patch 2210 with respect to the limbs 2212*a*, 2212*b*. In still other embodiments, the limbs 2212*a*, 2212*b* can be passed through the patch 2210 from the proximal-most end 2210*p* to the distal-most end 2210*d* by passing through the body while only entering and exiting the body one time, for instance when no bores 2214*a*, 2214*b* are provided. Of course, the limbs 2212*a*, 2212*b* do not necessarily have to extend all the way to the proximal-most or distal-most ends 2210*p*, 2210*d*, but instead can enter and or exit the self-deploying patch 2210 at some other location across its surface area. A person skilled in the art will recognize a variety of other ways by which the self-deploying patch 2210 can be associated with the limbs 2212*a*, 2212*b* without departing from the spirit of the present disclosure.

The self-deploying tissue augmentation patch 2210 can be threaded by hand on to the suture limbs 2212*a*, 2212*b*, either at the surgical site, or outside of the body. Alternatively, as shown in FIG. 9B, the threaders 2206*a*, 2206*b* can be operated to associate the suture limbs 2212*a*, 2212*b* with the self-deploying patch 2210, and thus including proximal handle portions 2208*a*, 2208*b*, intermediate elongate portions 2207*a*, 2207*b*, and distal suture-receiving ends 2209*a*, 2209*b*. Accordingly, the self-deploying tissue augmentation patch 2210 can be associated with the intermediate elongate portions 2207*a*, 2207*b*, as shown by passing the intermediate elongate portions 2207*a*, 2207*b* through the lumens 2214*a*, 2214*b*, and the limbs 2212*a*, 2212*b* can be coupled to the distal suture-receiving ends 2209*a*, 2209*b*. The proximal handle portions 2208*a*, 2208*b* can be grasped and pulled away from the tissue augmentation patch 2210 to advance the limbs 2212*a*, 2212*b* towards and into the self-deploying patch 2210. After the self-deploying patch 2210 has been successfully associated with the limbs 2212*a*, 2212*b*, the threaders 2206*a*, 2206*b* can be disassociated with the limbs 2212*a*, 2212*b* and the self-deploying tissue augmentation patch 2210 and can be either discarded or re-used, for example after being properly sterilized.

Similar to the earlier described tissue augmentation strips, associating the self-deploying tissue augmentation patch 2210 with the suture limbs 2212*a*, 2212*b* increases the footprint of the suture limbs 2212*a*, 2212*b* and may allow force applied to the tissue by the suture limbs 2212*a*, 2212*b* to be distributed over a larger amount of surface area, i.e., the surface area of the patch 2210. The increased distributed force of the self-deploying tissue augmentation patch 2210 may result in a reduced pressure peak on the soft tissue. Where the soft tissue has become degenerated due to injury or age, an increased tissue surface area coverage and a reduction in pressure can result in less chance of abrasion of the tissue. Further, the larger surface area of the self-deploying tissue augmentation patch 2210 can provide for a larger scaffold for new tissue to generate over the repair to further strengthen the repair site. The broader tissue coverage provided by the self-deploying patch 2210 may enhance the healing of otherwise compromised tissue and/or provide bulk to otherwise compromised or degenerate tissue and/or tendon.

Methods of Installation—Soft Tissue Repair with Self-Deploying Patches

Figure 9C:
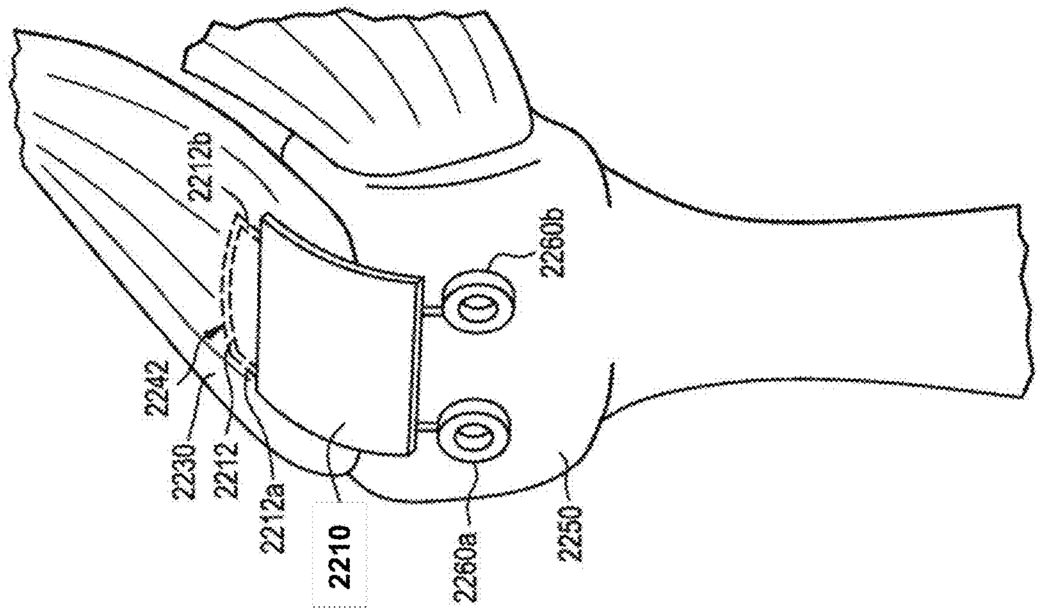
FIG. 9C is a schematic perspective view of one embodiment for installing the self-deploying tissue augmentation construct of FIG. 9A.
Figure 9D:
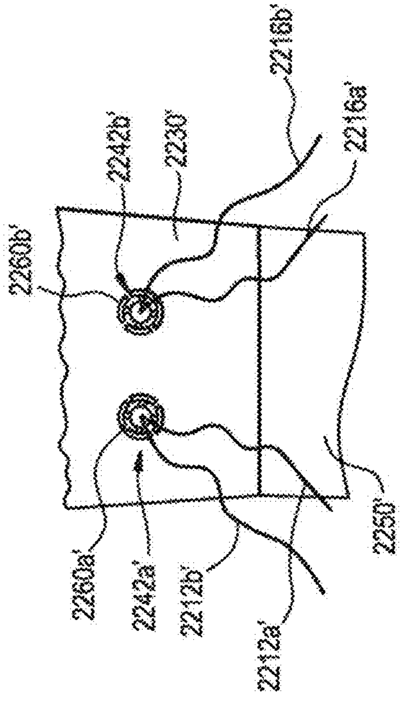
FIGS. 9D-9F are schematic sequential top views of one embodiment for installing a self-deploying tissue augmentation construct similar to that of FIG. 9A.
Figure 9E:
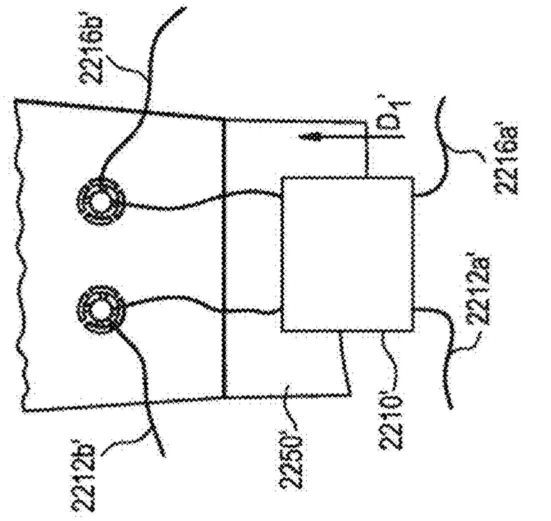
Figure 9F:
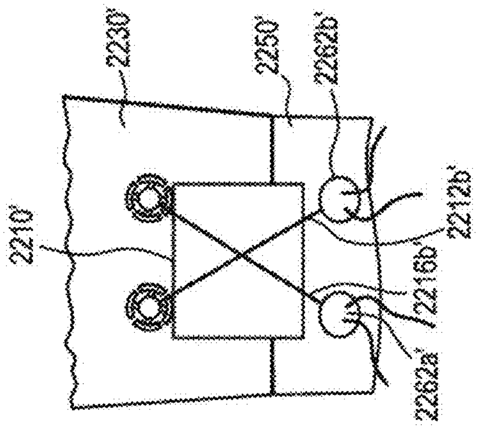

One method of installing a self-deploying tissue augmentation patch 2210 (e.g., graft) is illustrated in FIG. 9C, after the deployment of the patch in the surgical site. Deployment of the patch can include any and all of the methods and techniques disclosed herein, including deliver the self-deploying patch to the surgical site in a pre-deployment configuration and, once able, allowing or causing the self-deploying patch to be move to the post-deployment configuration. This can include, for example, initiating a movement of the self-deploying patch and/or de-coupling a holding suture or coupler that is holding the self-deploying patch in the pre-deployment configuration. Returning to FIG. 9C, the illustrated method provides for a piece of soft tissue 2230, e.g., rotator cuff, fixated to bone 2250. Either a single row or a double row repair can be used. Once the surgeon has access to the surgical site and the tissue, bone, and self-deploying tissue augmentation patch have been prepared according to accepted surgical techniques including those provided for herein, the surgeon can perform a tissue repair (not visible because it is underneath the self-deploying patch 2210) according to accepted surgical techniques. As shown in FIG. 9C, a suture 2212 extending from an anchor (not shown) used in the repair is installed into the tissue 2230 medially from the repair such that two suture limbs 2212*a*, 2212*b* extend out from the tissue 2230.

The self-deploying tissue augmentation patch 2210 can be threaded onto the suture limbs 2212*a*, 2212*b* using techniques provided for throughout the present disclosure, and subsequently advanced along the respective suture limbs 2212*a*, 2212*b* until it is proximate a medial stitch 2242. After the self-deploying patch 2210 has been installed on the suture limbs 2212*a*, 2212*b*, the free end of each suture limb 2212*a*, 2212*b* can be secured within the body. For example, the free ends of each suture limb 2212*a*, 2212*b* can be coupled to respective anchors 2260*a*, 2260*b* in a lateral row fixation. The suture limbs 2212*a*, 2212*b* can then be tightened to secure the self-deploying patch 2210 against the repair before the anchors 2260*a*, 2260*b* are fully fixed in the bone 2250.

The self-deploying patch 2210 can provide a greater footprint for the suture limbs 2212*a*, 2212*b* and a greater surface area to distribute the loading forces of the suture limbs 2212*a*, 2212*b* onto the soft tissue 2230. While the patient is healing from the procedure, the self-deploying patch can remodel into tendon-like tissue and integrate with the underlying native tissue. The additional coverage of tendon-like tissue across the soft tissue can increase the strength of the soft tissue to bone connection and may prevent further injury.

Another method of installing a self-deploying tissue augmentation patch 2210' is provided for in FIGS. 9D-9F, this time illustrating a piece of soft tissue 2230', e.g., rotator cuff, being fixated to bone 2250' using a double row repair. Once the surgeon has access to the surgical site and the tissue, bone, and self-deploying tissue augmentation patch have been prepared according to accepted surgical techniques including those provided for herein, the surgeon can install first and second medial anchors 2260*a'*, 2260*b'* in the bone 2250'. The first and second medial anchors 2260*a'*, 2260*b'* have sutures 2212', 2216' associated therewith. As shown in FIG. 9D, sutures 2212' and 2216' can have suture limbs 2212*a'*, 2212*b'* and 2216*a'*, 2216*b'* extending from the respective anchors 2260*a'* and 2260*b'*, with the limbs being threaded through the tissue 2230', for example using one or more medial stitches 2242*a'*, 2242*b'*. Deployment of the patch can include any and all of the methods and techniques disclosed herein, including deliver the self-deploying patch to the surgical site in a pre-deployment configuration and, once able, allowing or causing the self-deploying patch to be move to the post-deployment configuration. This can include, for example, initiating a movement of the self-deploying patch and/or de-coupling a holding suture or coupler that is holding the self-deploying patch in the pre-deployment configuration.

The self-deploying patch 2210' can have similar properties as the patch 2210 (or any of the self-deploying patches disclosed herein) and can be threaded onto the suture limbs 2212*a'*, 2216*a'* before or after deployment using techniques provided for throughout the present disclosure. The self-deploying patch 2210' can subsequently be advanced in the direction Di along the respective suture limbs 2212*a'*, 2216*a'*, as shown in FIG. 9E, until it is proximate the medial stitches 2242*a'*, 2242*b'*. After the patch 2210' has been installed on the suture limbs 2212*a'*, 2216*a'*, the free end of each of the suture limbs 2212*b'*, 2216*b'* can be placed over the patch 2210' in an X- or crossed configuration as shown in FIG. 9F. Then the suture limbs 2212*a'*, 2216*b'* can be installed into lateral anchor 2262*a'*, and the suture limbs 2212*b'*, 2216*a'* can be installed into lateral anchor 2262*b'* in a lateral row fixation. The suture limbs 2212*a'*, 2212*b'*, 2216*a'*, 2216*b'* can then be tightened to secure the soft tissue 2230' to the bone 2250' before the lateral anchors 2262*a'*, 2262*b'* are fully fixed in the bone 2250'. The same benefits described above with respect to the method of using the patch 2210 (and/or any of the self-deploying patches disclosed herein) are equally applicable to this embodiment of using the patch 2210'. Further, the crossed nature of the suture configuration provides additional stability for holding the tissue 2230' at the desired location with respect to the bone 2250'.

Tissue Augmentation Kits

The filaments, wires, and/or tissue staples, and self-deploying tissue augmentation constructs provided for herein can be included together as part of a soft tissue repair kit. Such a kit can also include components such as a threader, installation tool, bone anchors, and/or a bone drill. For example, one embodiment of a kit can include one or more self-deploying tissue augmentation constructs and one or more threaders. In some instances, the self-deploying tissue augmentation constructs can be pre-disposed on the threaders. The self-deploying tissue augmentation constructs can include any of the constructs provided for herein or otherwise derivable from the present disclosure. The threaders can include threaders known to those skilled in the art or otherwise derivable from the present disclosure.

The kit can also include other components used in conjunction with tissue augmentation constructs and threaders, including but not limited to one or more sutures, one or more installation tools, one or more implants in addition to the constructs (e.g., bone anchors, tissue staples), and/or one or more bone drills. The types and configurations of the filaments, constructs, installation tools (which can include threaders as stand-alone installation tools), and/or bone anchors can be varied, thus providing the user options for use in any surgical procedure. Accordingly, any combination of blocks can be mixed and matched by a surgeon, as desired and can depend, at least in part, on a variety of factors, including but not limited to the anatomy of the patient, the type of procedure being performed, and the preferences of the surgeon.

The threader and/or installation tool can be a single device used to associate self-deploying tissue augmentation constructs to limbs multiple times, or multiple threaders and tools can be provided to allow multiple construct-limb combinations to be formed or to allow for different configurations preferred by different users. The threader and/or installation tool can be specifically adapted to be used with particular self-deploying tissue augmentation constructs, procedures, and/or surgeon's preferences without departing from the spirit of the present disclosure.

To the extent implants such as anchors are provided as part of a kit, or used in conjunction with any of the disclosure provided for herein, the implants can be any type of implant known to those skilled in the art that are used for various types of tissue repair procedures. For bone anchors, the anchors can be of a hard construction or a soft construction, and in some instances they can be knotless anchors, meaning filaments associated therewith do not need to have knots tied by the surgeon during the surgical procedure to couple the tissue to the filament and/or the anchor. Some exemplary embodiments of hard suture anchors for use in the kits or more generally with the present disclosure include Healix Ti™ anchors that are commercially available from DePuy Synthes, as well as Healix Advance™ anchors, Helix Advance Knotless™ anchors, Healix BR™ anchors, Healix PEEK™ anchors, Healix Transtend™ anchors, Bioknotless® anchors, Gryphon® anchors, Fastin® anchors, Versalok® anchors, Microfix® anchors, Minilok™ anchors, Micro-Quickanchors® anchors, and Tacit® anchors, each of which is also commercially available from DePuy Mitek, Inc. Some exemplary embodiments of soft suture anchors for use in the kits or more generally with the present disclosure include those described in U.S. Pat. No. 9,345,567 of Sengun, the content of which is incorporated by reference herein in its entirety.

Materials for Forming Augmentation Constructs

The constructs discussed herein can be made of one or more biocompatible, bioresorbable materials so that after implantation into a patient to replace or repair connective tissue, the strip gradually degrades or remodels over time. The resorption profile of the constructs can be sufficiently long to reinforce and provide structure to tissue during the regeneration or healing process. A person skilled in the art can determine a suitable resorption profile, depending, at least in part, on the desired use of the construct, and can tailor the resorption profile by varying the materials used to form the construct.

While many different materials can be used to form the tissue augmentation constructs, either alone or in combination with other materials, in some instances the material is a biocompatible polymer. Exemplary embodiments of suitable biocompatible materials include, but are not limited to, synthetic polymers, natural polymers, and combinations of the two. As used herein, the term "synthetic polymer" refers to polymers that are not found in nature, even if the polymers are made from naturally occurring biomaterials. As used herein, the term "natural polymer" refers to polymers that are naturally occurring. In embodiments where the tissue augmentation constructs includes at least one synthetic polymer, suitable biocompatible synthetic polymers can include polymers selected from the group that includes aliphatic polyesters, poly(amino acids), copoly(ether-esters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly(ester urethanes), poly(propylene fumarate), poly(hydroxyalkanoate), polydioxanone, poly-hydroxybutyrate-co-hydroxyvalerate, polyamniocarbonate, polytrimethylene, polyoxaamides, elastomeric copolymers, and combinations or blends thereof. Suitable synthetic polymers for use in the tissue augmentation constructs can also include biosynthetic polymers based on sequences found in collagen, a collagen scaffold, pulverized collagen pieces, elastin, thrombin, silk, keratin, fibronectin, starches, poly(amino acid), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides, and combinations or blends thereof. The types of materials that can be used to construct tissue augmentation constructs, either wholly or in part, include non-absorbable polymers selected from the group that includes, but is not limited to, polyethylene, polypropylene, polyetheretherketone (PEEK), polytetrafluoroethylene, silicone, rubber, or other biocompatible non-absorbable polymers, and combinations thereof. Natural polymers for the use in self-deploying the tissue augmentation patch can be selected from the group that includes but is not limited to a fibrin-based material, collagen-based material, a hyaluronic acid-based material, a cellulose-based material, a silk-based material, a gelatin-based material, a glycoprotein-based material, a cellulose-based material, a polysaccharide-based material, a protein-based material, a fibronectin-based material, a chitin-based material, a pectin-based material, an elastin-based material, an alginate based material, a dextran-based material, an albumin-based material, a natural poly(amino acids) based material, a decellularized tissue, purified extracellular matrix (ECM), a demineralized bone matrix, and combinations thereof.

Still further, virtually any type of tissue can be used to form the tissue augmentation constructs, including but not limited to autograft tissue and allograft tissue, as well as human allogeneic tissue and xenogeneic tissue, which includes porcine, bovine, and equine among others. The tissue used can be selected from biological connective tissues that include ligament tissue, tendon tissue, a modeled tendon, skin tissue, muscle tissue, periosteal tissue, pericardial tissue, synovial tissue, dermal tissue, an acellular porcine dermal matrix, an acellular bovine dermal matrix, fascia, small intestine tissue, embryonic tissue, amniotic tissue, placental tissue, periodontal tissue, peritoneum tissue, vascular tissue, blood, and combinations thereof. The materials used to form the tissue augmentation constructs can be cross-linked and non-crosslinked, and any material provided for herein can be used in conjunction with other materials, whether synthetic, natural, or a combination thereof. Still further, the tissue augmentation constructs, and/or materials used to form the tissue augmentation constructs, can be treated with platelet-rich plasma (PRP), bone marrow, cells, and other bone and/or tissue growth-promoting materials.

The material used to form the tissue augmentation constructs can be made and/or formed, using a variety of techniques. These techniques include, but are not limited to, knitting them and weaving them. The overall construction of the materials can be described as being woven, knitted, non-woven, and/or a foam, among other constructions resulting from techniques known to a person skilled in the art. Further, a combination of techniques can be used for a single construct, and/or a portion thereof. The formation techniques can be used with materials, e.g., synthetic polymers and other materials provided for above, as well as tissue.

Methods of Manufacturing Self-Deploying Tissue Augmentation Grafts

The self-deploying tissue augmentation constructs provided for herein can be manufactured using a number of different techniques, some of which are provided for below. Other techniques known to those skilled in the art or developed subsequent to the present disclosure, particularly in view of the present disclosure, can also be used to manufacture the various configurations of tissue augmentation constructs disclosed.

The present disclosure provides for even more general techniques and methods that can be used to form the various self-deploying tissue augmentation constructs disclosed herein derivable from the present disclosure. The methods provided for in this section can be used as standalone methods, in conjunction with each other, and/or in conjunction with the other manufacturing techniques provided for in the present disclosure.

In some embodiments, the self-deploying constructs can be fully, or partially, manufactured by phase separation techniques, lyophilization, knitting, weaving, electrospinning, rapid prototyping (e.g., 3-D printing) or combinations of thereof. In order to facilitate tissue in growth, perforations can be created in the construct using thermal, electrical, or/and mechanical means, among others. For example, the perforations can be created by a laser or a sharp object such as a needle, punch, or die. The size of a perforation can be any suitable size, but preferably, the perforations are sized to allow tissue in-growth. More preferably, the perforations size can be approximately in the range of about 50 microns to about 2000 microns, and even more preferably, approximately in the range of about 50 microns to about 1000 microns.

In some embodiments, a biological tissue including, but not limited to, an allograft or xenograft tissue, may, optionally, be incorporated within the various tissue augmentation constructs, thus forming a two-layer construct. The combination of a biological tissue within the various tissue augmentation constructs can provide for enhanced biological performance and mechanical performance of a resulting construct.

Figure 10:
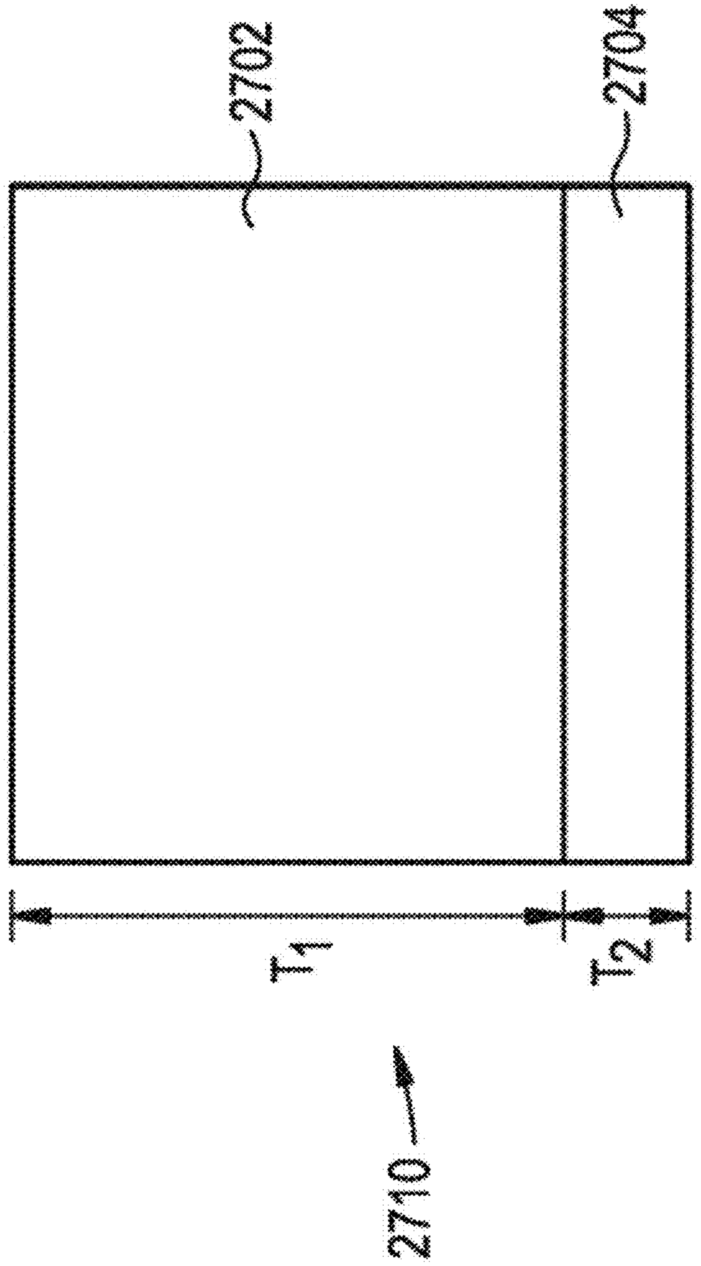
FIG. 10 is a side view of one embodiment of a self-deploying tissue augmentation construct.

For example, as shown in FIG. 10, a self-deploying construct 2710 (as shown a patch or scaffold, which is described in greater detail herein) can include a reconstituted collagen matrix or a biodegradable polymer, 2702 or any of the other materials described herein for use in a tissue augmentation construct (e.g., autograft, xenograft, pulverized collagen pieces, porcine dermis, etc.), and a biological component, such as an extracellular matrix (ECM) 2704, attached to one side of the matrix 2702 using techniques known to those skilled in the art. The reconstituted collagen matrix or biodegradable polymer can be, or can be part of, a first layer, and the biological component can be, or can be part of, a second layer, with a thickness and a surface area of the first layer being larger, and as shown substantially larger, than a thickness and a surface area of the second layer. In other embodiments, the biological component, e.g., the ECM 2704, can be disposed on opposed sides of the matrix 2702 and/or coated or soaked onto the matrix 2702. A person skilled in the art will recognize a number of different attachment options that can be used to couple the ECM(s) 2704 to the matrix 2702, including but not limited to gluing and stitching. The inclusion of the ECM 2704 or other biological component can help integrate the augmentation construct with the tissue with which the construct is being used. In one embodiment, the matrix 2702 can have a thickness Ty approximately in the range of about 1 millimeter to about 4 millimeters, and the ECM layer can have a thickness approximately in the range of about 80 microns to about 3 millimeters.

In some embodiments, a biological component can be coated onto the self-deploying tissue augmentation construct, or incorporated in the tissue augmentation construct. If a biological component is coated onto the tissue augmentation construct, the biological component is preferably associated with at least a portion of the construct. For example, the biocompatible construct can include an adhesion agent for anchoring the suspension of the biological component to a scaffold. The adhesion agent can be an anchoring agent, a cross-linking agent (i.e., chemical or physical), and combinations thereof. Suitable anchoring agents can include, for example, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

Cross-linking can be achieved using physical means and chemical agents. Examples of chemical agents used to cross-link can include dehydrothermal (DHT) treatment, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hexamethylene diisocyanate, 1-Ethyl-3-[3-dimethylaminopropyl]carbodiimide hydrochloride (EDC or EDAC), hydroxychloride, N-hydroxysuccinimide, light (e.g., blue light and UV light), pH, temperature, and combinations thereof.

The biological components can be one or more effectors that promote healing and/or regeneration of the affected tissue at the site of injury. The biological component of a construct can include heterologous or autologous growth factors, proteins, matrix proteins, peptides, antibodies, antibiotics, anti-inflammatories, therapeutic agents, chemotactic agents, antimicrobial agents, antibiotics, anti-inflammatory agents, compounds that minimize or prevent adhesion formation, compounds or agents that suppress the immune system, cell attachment mediators, biologically active ligands, integrin binding sequence, enzymes, cytokines, glycosaminoglycans, polysaccharides, viruses, virus particles, nucleic acids, analgesics, cells, platelets, platelet rich plasma (PRP), minced extracellular particles, minced tissue fragments, hydroxyapatite, tricalcium phosphate, bioactive glass, biphasic calcium phosphate, calcium sulfate, other bone and/or tissue growth-promoting materials, and combinations thereof.

As described herein, in some embodiments the tissue augmentation construct can have one or more through holes or bores extending therethrough. The through hole(s) can be a slit or a passage with different cross-sectional shapes, for example, circular, elliptical, square, rectangular, etc. The through hole(s) can be created by any tool that can remove materials including mechanical, thermal, or electrical tools.

Alternatively, the through hole(s) can be a slit(s) that can be created by any tool that results in the separation of two surfaces.

In some embodiments, the self-deploying construct can be made of more than one layer. The layers of the construct can be made of the same material or different materials. The layers can be bonded or fused together using sutures, mechanical, electrical, and chemical fastening techniques. Examples of bonding or fusing can include, for example, tissue welding, staples, rivets, tissue tacks, darts, screws, pins, arrows, cross-linking, vacuum pressing, compression, compression combined with dehydration, vacuum pressing combined with dehydration, or a biological adhesive or a combination of thereof. Dehydration in this context can include, for example, freeze-drying (i.e., lyophilization). Biological adhesives can include, for example, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PPP, Matrigel, Monostearoyl Glycerol co-Succinate (MGSA), Monostearoyl Glycerol co-Succinate/polyethylene glycol (MGSA/PEG) copolymers, laminin, elastin, hyaluronic acid, proteoglycans, and combinations thereof.

In some embodiments the construct can include a reinforcing material. The reinforcing material can be comprised of any absorbable or non-absorbable textile having, for example, woven, knitted, warped knitted (i.e., lace-like), non-woven, and braided structures. In one embodiment, the reinforcing material can have a mesh-like structure. Mechanical properties of the material can be altered by changing the density or texture of the material, the type of knit or weave of the material, the thickness of the material, or by embedding particles in the material.

Mechanical properties of the reinforcing material can additionally be altered by creating sites within the construct where fibers are physically bonded with each other or physically bonded with another agent, such as, for example, an adhesive or a polymer. The fibers used to make the reinforcing component can be, for example, monofilaments, yarns, threads, braids, or bundles of fibers. These fibers can be made of any biocompatible material including, but not limited to, bioabsorbable materials such as polylactic acid (PLA), polyglycolic acid (PGA), polycaprolactone (PCL), polydioxanone (PDO), trimethylene carbonate (TMC), copolymers or blends thereof. The fibers can also be made from any biocompatible materials based on natural polymers including silk and collagen-based materials. Alternatively, the fibers can also be made of any biocompatible fiber that is nonresorbable, such as, for example, polyethylene, nylon, polyester, polyethylene terephthalate, poly(tetrafluoroethylene), polycarbonate, polypropylene, polyurethane, and poly(vinyl alcohol).

In another embodiment, the construct may incorporate hydroxyapatite, tricalcium phosphate, Bioglass, biphasic calcium phosphate, calcium sulfate, other bone-promoting materials within the whole construct or localized in a portion of the construct where bone regeneration is desired. Bioglass is a silicate containing calcium phosphate glass, or calcium phosphate glass with varying amounts of solid particles added to control resorption time. Bioglass is one example of materials that can be spun into glass fibers and used as a reinforcing material. Bioglass can also be incorporated into the construct in a powder form. Suitable solid particles may be added include iron, magnesium, sodium, potassium, and combinations thereof.

In some embodiments, both the biocompatible construct and the reinforcing material may be formed from a thin, perforation-containing elastomeric sheets with pores or perforations to allow tissue in-growth. A sheet can be made of blends or copolymers of polylactic acid (PLA), polyglycolic acid (PGA), polycaprolactone (PCL), and polydioxanone (PDO).

The construct can be formed partially or completely from a polymeric foam component, having pores with an open cell pore structure. The pore size can vary, but preferably, the pores are sized to allow tissue in-growth. In some embodiments, the pore size is approximately in the range of about 40 microns to about 1000 microns, and in other embodiments, the pore size is approximately in the range of about 50 microns to about 500 microns. The polymeric foam component can be made from natural or/and synthetic materials, such as reconstituted collagen. The polymeric foam can be non-crosslinked or crosslinked. The polymeric foam component can, optionally, contain a reinforcing component, such as for example, textiles as discussed above. In some embodiments, the polymeric foam component can contain a reinforcing component which can be integrated with the reinforcing component such that the pores of the foam component penetrate the mesh of the reinforcing component and interlock with the reinforcing component.

In some embodiments the polymeric foam component of the tissue implant may be formed as a foam by a variety of techniques well known to those having skill in the art. For example, the polymeric starting materials may be foamed by lyophilization, supercritical solvent foaming, which is described at least in European Patent Application No. 464,163, the contents of which is incorporated by reference herein in its entirety, gas injection extrusion, gas injection molding or casting with an extractable material (e.g., salts, sugar, or similar suitable materials).

A polymeric foam component of engineered tissue repair implant devices of the present disclosure may be made by a polymer-solvent phase separation technique, such as lyophilization. A polymer solution can be separated into two phases by any one of the four techniques: (a) thermally induced gelation/crystallization; (b) non-solvent induced separation of solvent and polymer phases; (c) chemically induced phase separation; and (d) thermally induced spinodal decomposition. The polymer solution can be separated in a controlled manner into either two distinct phases or two bi-continuous phases. Subsequent removal of the solvent phase usually leaves a porous structure with a density less than the bulk polymer and pores in the micrometer ranges. Additional information about the solvent phase is provided in Microcellular Foams via Phase Separation, J. Vac. Sci. Technol., A. T. Young, Vol. 4(3), May/June 1986, the contents of which is incorporated by reference herein in its entirety.

The steps involved in the preparation of these foams include, for example, choosing the right solvents for the polymers to be lyophilized and preparing a homogeneous solution. Next, the polymer solution can be subjected to a freezing and vacuum drying cycle. The freezing step phase can separate the polymer solution and vacuum drying step can remove the solvent by sublimation and/or drying, leaving a porous polymer structure or an interconnected open cell porous foam. Suitable solvents that may be used in the preparation of the foam component can include, for example, formic acid, ethyl formate, acetic acid, hexafluoroisopropanol (HFIP), cyclic ethers (e.g., tetrahydrofuran (THF), dimethylene fluoride (DMF), and polydioxanone (PDO)), acetone, acetates of C2 to C5 alcohols (e.g., ethyl acetate and t-butylacetate), glyme (e.g., monoglyme, ethyl glyme, diglyme, ethyl diglyme, triglyme, butyl diglyme and tetraglyme), methylethyl ketone, dipropyleneglycol methyl ether, lactones (e.g., γ-valerolactone, δ-valerolactone, β-butyrolactone, γ-butyrolactone), 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methylpyrrolidone, dimethylformamide, chloroform, 1,2-dichloromethane, morpholine, dimethylsulfoxide, hexafluoroacetone sesquihydrate (HFAS), anisole, and mixtures thereof. Among these solvents, one exemplary solvent is 1,4-dioxane. A homogeneous solution of the polymer in the solvent is prepared using standard techniques.

The applicable polymer concentration or amount of solvent that may be utilized can vary with each system. In one embodiment, the amount of polymer in the solution can vary from about 0.5% to about 90% by weight. In another embodiment, preferably, the amount of polymer in the solution can vary from about 0.5% to about 30% by weight. The amount of polymer in the solution can vary depending on factors such as the solubility of the polymer in a given solvent and the final properties desired in the foam.

In embodiments of the construct that include a polymeric foam, solids may be added to the polymer-solvent system to modify the composition of the resulting polymeric foam surfaces. As the added particles settle out of solution to the bottom surface, regions will be created that will have the composition of the added solids, not the foamed polymeric material. Alternatively, the added solids may be more concentrated in desired regions (i.e., near the top, sides, or bottom) of the resulting tissue augmentation construct, thus causing compositional changes in all such regions. For example, concentration of solids in selected locations can be accomplished by adding metallic solids to a solution placed in a mold made of a magnetic material (or vice versa).

A variety of types of solids can be added to the polymer-solvent system. In one embodiment, the solids are of a type that will not react with the polymer or the solvent. The added solids can have an average diameter of less than about 2 millimeters. In other embodiments, added solids can have an average diameter of about 50 microns to about 1000 microns. The solids can be present in an amount such that they will constitute from about 1 volume to about 50 volume percent of the total volume of the particle and polymer-solvent mixture (wherein the total volume percent equals 100 volume percent).

Exemplary solids include, for example, particles of demineralized bone, calcium phosphate particles, Bioglass particles, calcium sulfate, or calcium carbonate particles for bone repair, leachable solids for pore creation and particles of bioabsorbable natural polymers, bioabsorbable synthetic polymers, non-bioabsorbable materials, minced extracellular particles, minced tissue fragments, or any biocompatible materials that is not soluble in the solvent system.

Exemplary leachable solids include, for example, nontoxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water soluble proteins (e.g., gelatin and agarose). Leachable materials can be removed by immersing the foam with the leachable material in a solvent in which the particle is soluble for a sufficient amount of time to allow leaching of substantially all of the particles. The solvent can be chosen so that it does not dissolve or detrimentally alter the foam. One preferred embodiment can include water as the extraction solvent, for example distilled-deionized water. Such a process is described further in U.S. Pat. No. 5,514,378, the contents of which is incorporated by reference herein in its entirety. Preferably the foam will be dried after the leaching process is complete at low temperature and/or vacuum to minimize hydrolysis of the foam unless accelerated absorption of the foam is desired.

Non-bioabsorbable materials can include, for example, bioinert ceramic particles (e.g., alumina, zirconia, and calcium sulfate particles), polymers such as polyethylene, polyvinylacetate, polymethylmethacrylate, polypropylene, poly(ethylene terephthalate), silicone, polyethylene oxide, polyethylene glycol, polyurethanes, polyvinyl alcohol, natural polymers (e.g., cellulose particles, chitin, and keratin), and fluorinated polymers and copolymers (e.g., fluoride, polytetrafluoroethylene, and hexafluoropropylene). In one embodiment, it is possible to add solids (e.g., barium sulfate) that will render the tissue implants radio opaque. Those solids that may be added also include those that will promote tissue regeneration or healing, as well as those that act as buffers, reinforcing materials or porosity modifiers.

As discussed above, polymeric foam components can contain a reinforcing component, which can be useful for helping with the function of a wire in a self-deploying patch according to aspects of the present disclosure. The construct can be made by injecting, pouring, or otherwise placing, the appropriate polymer solution into a mold set-up comprised of a mold and the reinforcing elements of the present disclosure. The mold set-up can be cooled in an appropriate bath or on a refrigerated shelf and then lyophilized, thereby providing a reinforced construct.

In embodiments that utilize a polymeric foam, one or more of the biological components provided for throughout the present disclosure can be added either before or after the lyophilization step. In the course of forming the polymer foam component, it can be beneficial to control the rate of freezing of the polymer-solvent system. The type of pore morphology that is developed during the freezing step is a function of factors such as the solution thermodynamics, freezing rate, temperature to which it is cooled, concentration of the solution, and whether homogeneous or heterogeneous nucleation occurs. The orientation of the polymeric fibers can be regulated be controlling the pore orientation. The pores orientation in the polymeric form component can be customized, for example, by controlling the temperature gradient induced during the freezing cycle. Controlling the orientation of fibers can result in an improvement in the mechanical properties in the direction that the fibers are oriented.

The required general processing steps for a construct that uses polymeric foam can include the selection of the appropriate materials from which the polymeric foam will be made. The processing steps can additionally include selection of the materials of the reinforcing components if used. If a mesh reinforcing material is used, the proper mesh density should be selected. Further, the reinforcing material should be properly aligned in the mold, the polymer solution should be added at an appropriate rate and, preferably, into a mold that is tilted at an appropriate angle to avoid the formation of air bubbles, and the polymer solution must be lyophilized.

In embodiments that utilize a mesh reinforcing material in a polymeric foam, for example, the reinforcing mesh should be selected to be of a certain density. That is, the openings in the mesh material should not be so small so as to impede proper bonding between the foam and the reinforcing mesh as the foam material and the open cells and cell walls thereof penetrate the mesh openings. Without proper bonding the integrity of the layered structure can be compromised, leaving the construct fragile and difficult to handle. The density of the mesh can determine the mechanical strength of the construct. The density of the mesh can vary according to the desired use for tissue repair. In addition, the type of weave used in the mesh can determine the directionality of the mechanical strength of the construct, as well as the mechanical properties of the reinforcing material, such as for example, the elasticity, stiffness, burst strength, suture retention strength, and ultimate tensile strength of the construct. By way of non-limiting example, the mesh reinforcing material in a foam-based biocompatible construct of the present disclosure can be designed to be stiff in one direction, yet elastic in another, or alternatively, the mesh reinforcing material can be made isotropic.

During lyophilization of the reinforced foam in those embodiments that utilize a mesh reinforcing material in a polymeric foam, several parameters and procedures can be helpful to produce implants with the desired integrity and mechanical properties. For example, if reinforcement material is used, it can be beneficial to maintain the reinforcement material substantially flat when placed in the mold. To ensure the proper degree of flatness, the reinforcement (e.g., mesh) can be pressed flat using a heated press prior to its placement within the mold. Further, in the event that reinforcing structures are not isotropic, it can be desirable to indicate this anisotropy by marking the construct to indicate directionality. The marking can be accomplished by embedding one or more indicators, such as dyed markings or dyed threads, within the woven reinforcements. The direction or orientation of the indicator can, for example, indicate to a surgeon the dimension of the implant in which physical properties are superior.

In embodiments that utilize polymeric foam, as noted above, the manner in which the polymer solution is added to the mold prior to lyophilization can help contribute to the creation of a tissue implant with adequate mechanical integrity. Assuming that a mesh reinforcing material will be used, and that it will be positioned between two thin (e.g., approximately 0.75 millimeters) shims, the mesh can be positioned in a substantially flat orientation at a desired depth in the mold. The polymer solution can be poured in a way that allows air bubbles to escape from between the layers of the foam component. The mold can be tilted at a desired angle and pouring is effected at a controlled rate to best prevent bubble formation. A number of variables will control the tilt angle and pour rate. For example, the mold should be tilted at an angle of greater than about one degree to avoid bubble formation. In addition, the rate of pouring should be slow enough to enable any air bubbles to escape from the mold, rather than to be trapped in the mold.

In those embodiments that utilize a mesh reinforcing material in a polymeric foam, the density of the mesh openings can be an important factor in the formation of the construct with the desired mechanical properties. For example, a low density, or open knitted mesh material, can be used. One example of such a material is a 90:10 copolymer of glycolide and lactide, sold under the tradename VICRYL, which is available from Ethicon, Inc. of Somerville, New Jersey. One exemplary low density, open knitted mesh is Knitted VICRYL VKM-M, which is also available from Ethicon, Inc. of Somerville, New Jersey. Other materials can include but are not limited to polydioxanone and a 95:5 copolymer blend of lactide and glycolide.

In embodiments that utilize a polymeric foam, a through opening can be created by placing a rod in the polymeric foam solution/slurry before it has set. After the polymeric form is formed, the rod can be removed. For example, if the polymeric foam is made by lyophilization, the rod is removed after the freeze and vacuum drying cycle. The rod can have any desired shape.

The polymeric foam component can, optionally, contain one or more layers made of the materials discussed above. In one embodiment, the foam component can be integrated with the material(s) by creating pores in the materials and then the polymeric foam component penetrate the pores created in the materials(s) and interlock with the material(s). In another embodiment, pores are formed in materials of two layers, and the two layers are put together to best align the pores. The two layer combination can be placed in a polymeric solution or slurry, and the polymeric foam can be formed by one of the methods provided for herein or otherwise known to those skilled in the art.

Figure 11A:
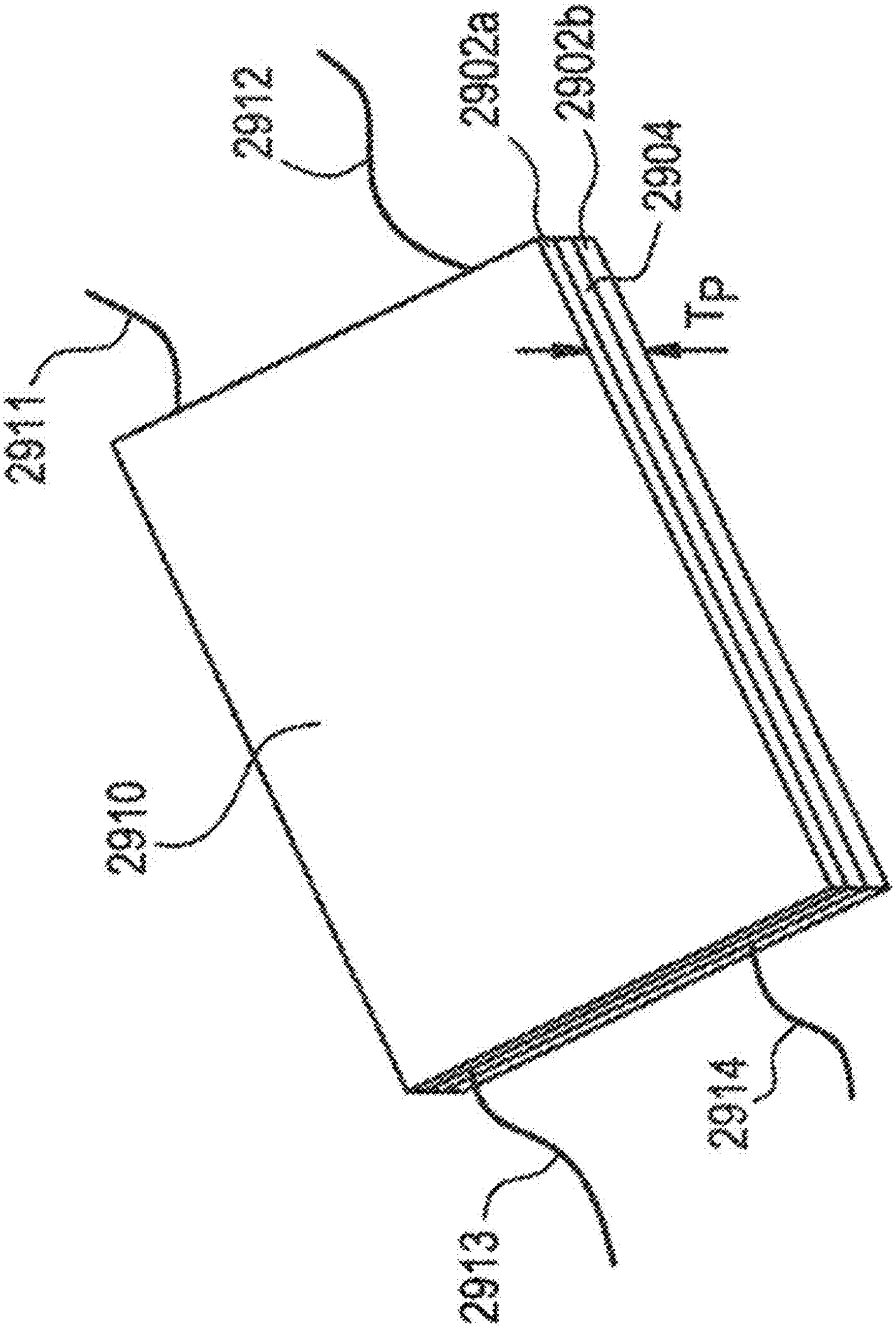
FIG. 11A is a perspective view of another embodiment of a self-deploying tissue augmentation construct.
Figure 11B:
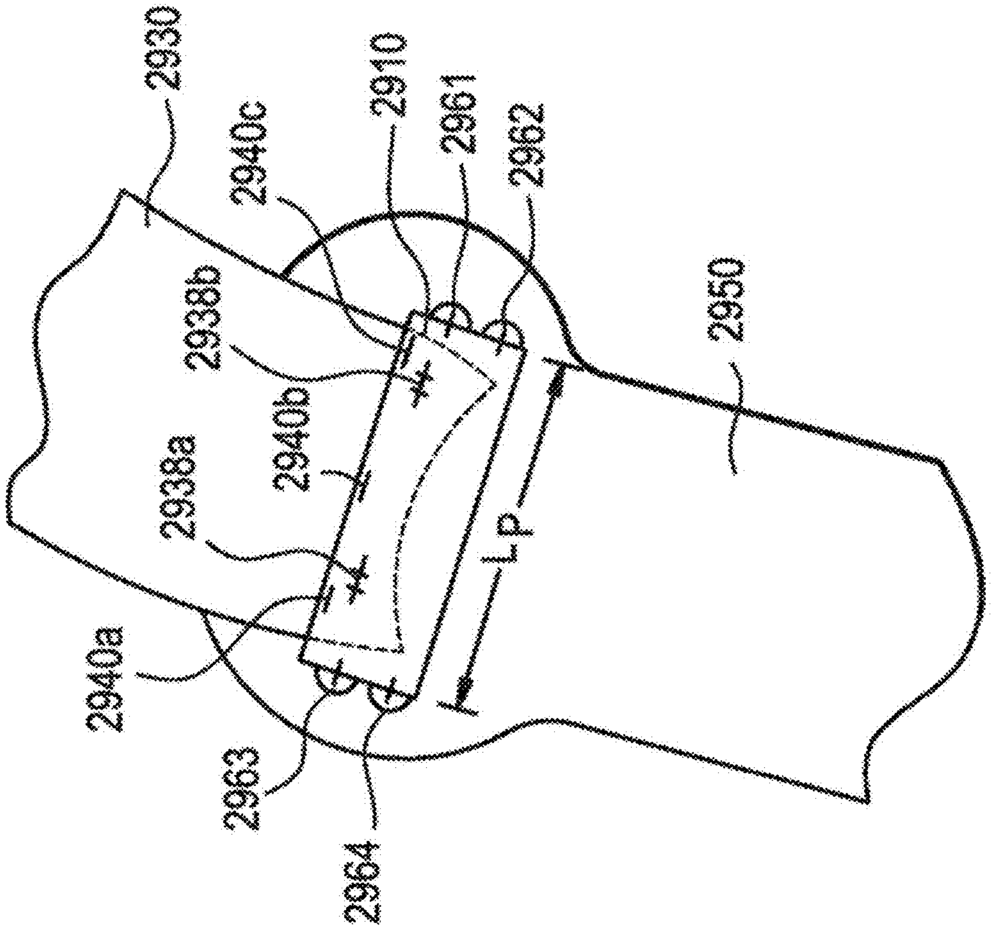
FIG. 11B is a perspective view of the self-deploying tissue augmentation construct of FIG. 11A installed at a surgical site.

In some embodiments, a self-deploying construct can be formed from an expanding media that can advantageously provide added compression at the repair site. One non-limiting example of such a self-deploying construct 2910 is shown in FIGS. 11A-11B, in which the self-deploying construct is a patch or graft. For example, the construct 2910 can be formed from a woven or braided mesh having a core 2904 surrounded or sandwiched between two layers 2902*a*, 2902*b*, which can improve the deployment performance of a wire in a self-deploying patch. The two layers 2902*a*, 2902*b* can be referred to as a jacket. The core 2904 can be made from a variety of materials that are capable of expanding, such as silicone loaded with salt, sodium polyacrylate, polyacrylamide copolymer, polyurethanes, and other absorbent polymers and hydro gels, while the jacket 2902*a*, 2902*b* can be more rigid so that the core can compress against the jacket as it expands in use. Non-limiting exemplary materials that can be used to form the jacket 2902*a*, 2909*b* include fabric and filament such as polyethylene, polypropylene, polyester, poly(ethylene terephthalate), nylon, polyurethanes and silk. Further non-limiting exemplary materials that can be used to form the jacket 2902*a*, 2902*b* include bioabsorbable materials such as polylactic acid (PLA), polyglycolic acid (PGA), polycaprolactone (PCL), polydioxanone (PDO), trimethylene carbonate (TMC), copolymers or blends thereof. Some materials that can be used in conjunction with the construct include, but are not limited to, those disclosed and provided for in U.S. Pat. No. 8,870,915, entitled "Joining Element," the contents of which is incorporated by reference herein in its entirety. The self-deploying construct 2910 can have a length $L_P$, as shown in FIG. 11B, and a thickness $T_P$, as shown in FIG. 11A, and can include at least one suture limb 2911 for affixing the construct to one or more repair sites. In the illustrated example the self-deploying construct 2910 includes four suture limbs 2911, 2912, 2913, 2914 associated with it. The limbs can be from the same or different sutures.

In use, as shown in FIG. 11B, the self-deploying construct 2910 can be placed over the repair sites 2938*a*, 2938*b*, and the suture limbs 2911, 2912, 2913, 2914 can be fixed within respective anchors 2961, 2962, 2963, 2964. As with other disclosures, the repairs associated with the repair sites 2938*a*, 2938*b* can be any type of repair provided for herein or otherwise known to those skilled in the art. The self-deploying construct 2910 can be further affixed to a location medial of the repairs 2938*a*, 2938*b* with sutures, staples, or other devices and components used to fixate tissue with respect to bone. As shown, sutures 2940*a*-2940*c* provide the fixation. The self-deploying construct 2910 can be exposed to an aqueous solution, for example after installation, such that the silicone and salt filled core can absorb the fluid to cause the construct to expand in at least one dimension and contract in at least one other dimension based on the configuration of the construct 2910. In the illustrated example, the expansion causes the self-deploying construct 2910 to increase in thickness $T_P$ while contracting and decreasing across its length $L_P$. The decrease in the length $L_P$ after the self-deploying construct 2910 is installed can increase the compressive forces to the soft tissue 2930 to bring the tissue into more uniform contact with the bone 2950 due, at least in part, to the limited space for fixation of the construct 2910, the configuration of the self-deploying construct 2910, and the surface geometry of the attachment site. One skilled in the art will appreciate that a configuration of a self-deploying construct having a core, capable of expanding, sandwiched between layers or a jacket can be used with other construct configurations provided for herein, including those that are not necessarily a patch or graft, to provide for added compressive forces at repair sites.

Unless specified otherwise, any of the materials, and any of the techniques disclosed for forming materials, can be used in conjunction with any of self-deploying constructs provided for herein. This includes any combination of materials. Likewise, the manufacturing techniques disclosed can generally be used, or adapted to form the various self-deploying constructs provided for herein. The use of materials and manufacturing techniques for various self-deploying tissue augmentation constructs is within the spirit of the present disclosure.

Self-Deploying Tissue Augmentation Constructs—Additional Details

A person skilled in the art will recognize that in any embodiments in which multiple threaders are used in conjunction with a construct, a location of the proximal and distal ends of the threaders can be different than the illustrated embodiments, depending, at least in part, on the type of procedure being performed, the components being used to perform the procedure, and the preferences of the user. Thus, in any illustrated embodiments, locations of the proximal and distal ends of the threaders can be switched in other embodiments. Further, in any of the illustrated embodiments, a location of any threader with respect to a tissue augmentation construct prior to using the threaders to associate a suture with the tissue augmentation construct is considered a pre-installation configuration, and after a threader has been used to associate a suture with a tissue augmentation construct and subsequently removed, such a configuration is considered a post-installation configuration.

Many more configurations of self-deploying grafts and sutures are within the scope of the present disclosure. Configurations can be derived from making adjustments to various parameters or variables provided for and discussed throughout the present application. Some parameters or variables that can be changed to provide for various configurations include: (1) the number of layers used to form the graft (e.g., one layer, two layers); (2) the orientation of one or more flexible resilient wires with respect to each other and the graft; (3) a location of a set of suture limbs with respect to the patch (e.g., on top of the patch, through the graft); (4) the inclusion of one or more "stitches" or "loops" to fixate the wire with respect to the graft; (5) whether one or more flexible resilient members are disposed in lumens formed in the graft or are disposed in structures (e.g., catches, loops, stitches) across a surface of the graft; (6) at least a portion of the one or more flexible resilient members are exposed at a surface of the graft; (7) a shape of the one or more flexible resilient members with respect to a shaft of the graft, either in the; and/or (8) the shapes of the self-deploying graft in the first state and in the second state.

One skilled in the art will understand that the various parameters can be mixed and matched to arrive at a large number of configurations, many of which are not explicitly illustrated herein, but are derivable based on the understanding provided about each of the variables and the constructs more generally as disclosed in the present application. To assist in understanding some of the options associated with the above-listed parameters, some parameter are discussed in more detail below. However, it is contemplated that the instant disclosure encompasses each discrete combination of parameters in conjunction with many of the different patch configurations provided for in the present disclosure.

One parameter that can be changed to achieve various self-deploying patch configurations is the number of layers that form each graft. For example, each self-deploying patch can include a single layer of material with lumens being formed in the single layer for disposing suture limbs and/or wires therethrough. The single layer can include a tissue-facing or tissue-engaging surface, also referred to herein as a bottom side of the self-deploying patch, and a second surface that is opposed to the tissue-facing surface, also referred to herein as a top side of the patch. Alternatively, each self-deploying patch can include two or more layers of material stitched together to form a single patch with lumens being formed between two or more layers for disposing suture limbs and/or wires therethrough. When a second layer is used, each layer includes a tissue-facing surface and a second surface that is opposed to the tissue-facing surface. In such embodiments, the tissue-facing surface of the patch is formed by the tissue-facing surface of the bottom, or more distal, patch, and the second surface of the patch that is opposed to the tissue-facing surface is formed by the second surface of the top, or more proximal, patch. Even in patches that include multiple layers, a lumen can be formed in a single layer. In embodiments where the patch includes at least two layers, the stitching can form lumens. As discussed above, in embodiments where two or more layers of material are used, each layer can be, but does not have to be, formed from different materials to provide a variety of advantages, including but not limited to: the overall thickness of the patch configuration may not limited by a biological source; a level of cellular activity can be controlled (e.g., a high tissue integration layer on a tissue facing side and an adhesion barrier layer on the opposite side); and/or other material characteristics can be varied between each layer (e.g., toughness, biologic/synthetic, thick/thin, high-/low-porosity, etc.).

Notably, most any of the aforementioned parameters or variables can be mixed and matched in one or more patch configurations without departing from the spirit of the present disclosure. Accordingly, there are many different configurations that can result from the present disclosure. The term "most any" is used because a person skilled in the art will recognize that, depending on the value of some of these parameters, some of the other parameters may not be adjustable, and a person skilled in the art will recognize as such in view of the present disclosure and the skilled person's knowledge. Each of the illustrated configurations can be used in conjunction with various procedures.

Examples of the disclose include the following:

1. A method of soft tissue repair, comprising:

introducing a self-deploying tissue augmentation patch to a surgical repair site, the patch being introduced in a pre-deployment state and the self-deploying patch having a flexible resilient member that is configured to assist in the deployment of the self-deploying patch from the pre-deployment state to the post-deployment state;

after introducing the self-deploying tissue augmentation patch to the surgical site, initiating at least a deployment operation of the self-deploying tissue augmentation patch, the deployment operation moving the self-deploying tissue augmentation patch from the pre-deployment to the post-deployment state; and coupling the self-deploying tissue augmentation patch in the post-deployment state to tissue in the surgical repair site, wherein the tissue augmentation patch in the post-deployment state defines a first length, a first width, and a first thickness, wherein the tissue augmentation patch in the pre-deployment state defines a second length, a second width, and a second thickness, at least one of the second length or second width being smaller than the respective first length or first width, and the second thickness being greater than the first thickness, wherein, in the pre-deployment state, at least a portion of the tissue augmentation patch is overlapping with a different portion of the tissue augmentation patch, and wherein, during at least a final portion of the movement from the pre-deployment state towards the post-deployment state, the flexible resilient member urges the movement of the tissue augmentation patch towards the post-deployment state.

2. The method of example 1, wherein, in the pre-deployment state, at least a portion of the flexible resilient member is overlapping with a different portion of the flexible resilient member.

3. The method of examples 1 or 2, wherein the flexible resilient member comprises a wire.

4. The method of example 3, wherein the wire defines a shape memory that preferentially biases the wire to move the tissue augmentation patch towards the post-deployment shape.

5. The method of any of examples 1 to 4, wherein the flexible resilient member defines a first rounded closed curve in the post-deployment state and two or more second rounded closed curves in the pre-deployment state, the first curve having a maximum chord greater than a maximum chord of either of the two or more second rounded closed curves.

6. The method of any of examples 1 to 5, wherein the movement from the pre-deployment state towards the post-deployment state comprises a twisting movement and a folding movement of the tissue augmentation patch such that, in the pre-deployment state at least a portion of the tissue-facing surface is opposing a portion of the second surface.

7. The method of any of examples 1 to 6, wherein at least a portion of the flexible resilient member is embedded in the tissue augmentation patch.

8. The method of example 7, wherein a different portion of the flexible resilient member is exposed at an opening in the tissue-facing surface or the second surface.

9. The method of example 8, further comprising removing the flexible resilient member from the tissue augmentation patch via the opening after the self-deploying tissue augmentation patch is moved to the post-deployment state.

10. The method of any of examples 1 to 10, further comprising removing the flexible resilient member from the tissue augmentation patch in the post-deployment state.

11. The method of example 10, wherein the removing action occurs during or after coupling the self-deploying tissue augmentation patch in the post-deployment state to the tissue in the surgical repair site.

12. The method of any of examples 1 to 11, wherein introducing the self-deploying tissue augmentation patch to the surgical repair site further comprises providing an insertion force to the tissue augmentation patch by urging an insertion instrument against an exposed portion of the flexible resilient member.

13. The method of any of examples 1 to 12, wherein the second surface of the tissue augmentation patch comprises a plurality of loops or pockets through which the flexible resilient member is disposed to couple the flexible resilient member with the tissue augmentation patch.

14. The method of any of examples 1 to 13, wherein the flexible resilient member defines a first end and a second end, the flexible resilient member further defining a closed curve such that the first is disposed adjacent to the second end, the second end and the first end being one of removably coupled or severably coupled together.

15. The method of any of examples 1 to 14, wherein the tissue augmentation patch comprises a one of a severable coupling or a removable coupling securing the tissue augmentation patch in the pre-deployment state, the method further including removing or severing the coupling.

16. The method of example 15, wherein the flexible resilient member is configured to urge the tissue augmentation patch in the pre-deployment state towards the post-deployment state against the coupling such that one or severing or removing the coupling initiates movement of the tissue augmentation patch towards the post-deployment state.

17. The method of any of examples 1 to 16, wherein the flexible resilient member urges the tissue augmentation patch in the pre-deployment state towards the post-deployment state against the coupling such that the flexible resilient member in the pre-deployment state initiates movement of the tissue augmentation patch towards the post-deployment state.

18. The method of any of examples 1 to 17, wherein the tissue augmentation patch comprises at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, or fascia.

19. The method of example aim 19, wherein the tissue augmentation patch comprises collagen.

20. A self-deploying soft tissue repair system, comprising:

a tissue augmentation patch having:

a first layer of material;

a tissue-facing surface; and a second surface opposed to the tissue-facing surface; and a flexible resilient member coupled to the tissue augmentation patch, wherein the tissue augmentation patch and the flexible resilient member together define a post-deployment state in which the tissue augmentation patch defines a first length, a first width, and a first thickness, wherein the tissue augmentation patch and the flexible resilient member together define a pre-deployment state in which the tissue augmentation patch defines a second length, a second width, and a second thickness, at least one of the second length or second width being smaller than the respective first length or width, and the second thickness being greater than the first thickness, wherein, in the pre-deployment state, at least a portion of the tissue augmentation patch is overlapping with a different portion of the tissue augmentation patch, wherein the self-deploying soft tissue repair system is moveable between the pre-deployment state and the post-deployment state, and wherein, during a movement from the pre-deployment state towards the post-deployment state, the flexible resilient member is configured to complete the movement of the tissue augmentation patch to the post-deployment state.

21. The self-deploying soft tissue repair system of example 20, wherein, in the pre-deployment state, at least a portion of the flexible resilient member is overlapping with a different portion of the flexible resilient member.

22. The self-deploying soft tissue repair system of examples 20 or 21, wherein the flexible resilient member comprises a wire.

23. The self-deploying soft tissue repair system of example 22, wherein the wire defines a shape memory that preferentially biases the wire to move the tissue augmentation patch towards the post-deployment shape.

24. The self-deploying soft tissue repair system of any of examples 20 to 23, wherein the flexible resilient member defines a first rounded closed curve in the post-deployment state and two or more second rounded closed curves in the pre-deployment state, the first curve having a maximum chord greater than a maximum chord of either of the two or more second rounded closed curves.

25. The self-deploying soft tissue repair system of any of examples 20 to 24, wherein the movement from the pre-deployment state towards the post-deployment state comprises a twisting movement and a folding movement of the tissue augmentation patch such that, in the pre-deployment state at least a portion of the tissue-facing surface is opposing a portion of the second surface.

26. The self-deploying soft tissue repair system of any of examples 20 to 25, wherein at least a portion of the flexible resilient member is embedded in the tissue augmentation patch.

27. The self-deploying soft tissue repair system of example 24, wherein a different portion of the flexible resilient member is exposed at an opening in one of the tissue-facing surface or the second surface.

28. The self-deploying soft tissue repair system of example 27, wherein the flexible resilient member is configured to be removed from the tissue augmentation patch via the opening.

29. The self-deploying soft tissue repair system of any of examples 20 to 28, wherein the second surface of the tissue augmentation patch comprises one of a plurality of loops or a plurality of pockets through which the flexible resilient member is disposed to couple the flexible resilient member with the tissue augmentation patch.

30. The self-deploying soft tissue repair system of any of examples 20 to 29, wherein the flexible resilient member defines a first end and a second end, the flexible resilient member further defining a closed curve such that the first is disposed adjacent to the second end, the second end and the first end being one of removably coupled or severably coupled together.

31. The self-deploying soft tissue repair system of any of examples 20 to 30, further comprises one of a severable coupling or a removable coupling securing the system in the pre-deployment state.

32. The self-deploying soft tissue repair system of example 31, wherein the flexible resilient member is configured to urge the system in the pre-deployment state towards the post-deployment state against the coupling such that one of severing the coupling or removing the coupling initiates movement of the system towards the post-deployment state.

33. The self-deploying soft tissue repair system of any of examples 20 to 32, wherein the flexible resilient member is configured to urge the system in the pre-deployment state towards the post-deployment state against the coupling such that the flexible resilient member in the pre-deployment state initiates movement of the system towards the post-deployment state.

34. The foldable soft tissue repair system of any of examples 20 to 33, wherein tissue augmentation patch comprises at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, or fascia.

35. The foldable soft tissue repair system of example 34, wherein the tissue augmentation patch comprises collagen.

One skilled in the art will appreciate further features and advantages of the present disclosure based on the above-described embodiments. Accordingly, the disclosure is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A method of soft tissue repair, comprising:

introducing a self-deploying tissue augmentation patch to a surgical repair site, the patch being introduced in a pre-deployment state and the self-deploying patch having a flexible resilient member that is configured to assist in the deployment of the self-deploying patch from the pre-deployment state to the post-deployment state;

after introducing the self-deploying tissue augmentation patch to the surgical site, initiating at least a deployment operation of the self-deploying tissue augmentation patch, the deployment operation moving the self-deploying tissue augmentation patch from the pre-deployment to the post-deployment state; and coupling the self-deploying tissue augmentation patch in the post-deployment state to tissue in the surgical repair site, wherein the tissue augmentation patch in the post-deployment state defines a first length, a first width, and a first thickness, wherein the tissue augmentation patch in the pre-deployment state defines a second length, a second width, and a second thickness, at least one of the second length or second width being smaller than the respective first length or first width, and the second thickness being greater than the first thickness, wherein moving the self-deploying tissue augmentation patch from the pre-deployment to the post-deployment state includes twisting opposite ends of the patch in opposite directions to create first and second portions separated by a twisted region having a width that is smaller than a width of either the first and second portions, and folding the first portion relative to the second portion about the twisted region to contact the first and second portions, wherein, in the pre-deployment state, at least a portion of the tissue augmentation patch is overlapping with a different portion of the tissue augmentation patch, and wherein, during at least a final portion of the movement from the pre-deployment state towards the post-deployment state, the flexible resilient member urges the movement of the tissue augmentation patch towards the post-deployment state.

2. The method of claim 1, wherein, in the pre-deployment state, at least a portion of the flexible resilient member is overlapping with a different portion of the flexible resilient member.

3. The method of claim 1, wherein the flexible resilient member comprises a wire.

4. The method of claim 3, wherein the wire defines a shape memory that preferentially biases the wire to move the tissue augmentation patch towards the post-deployment shape.

5. The method of claim 1, wherein the flexible resilient member defines a first rounded closed curve in the post-deployment state and two or more second rounded closed curves in the pre-deployment state, the first curve having a maximum chord greater than a maximum chord of either of the two or more second rounded closed curves.

6. The method of claim 1, wherein the tissue augmentation patch in the pre-deployment state includes at least a portion of a tissue-facing surface and a second surface that opposes the tissue-facing surface.

7. The method of claim 1, wherein at least a portion of the flexible resilient member is embedded in the tissue augmentation patch.

8. The method of claim 7, wherein a different portion of the flexible resilient member is exposed at an opening in a tissue-facing surface or a second surface that opposes the tissue-facing surface.

9. The method of claim 8, further comprising removing the flexible resilient member from the tissue augmentation patch via the opening after the self-deploying tissue augmentation patch is moved to the post-deployment state.

10. The method of claim 1, further comprising removing the flexible resilient member from the tissue augmentation patch in the post-deployment state.

11. The method of claim 10, wherein the removing action occurs during or after coupling the self-deploying tissue augmentation patch in the post-deployment state to the tissue in the surgical repair site.

12. The method of claim 1, wherein introducing the self-deploying tissue augmentation patch to the surgical repair site further comprises providing an insertion force to the tissue augmentation patch by urging an insertion instrument against an exposed portion of the flexible resilient member.

13. The method of claim 6, wherein the second surface of the tissue augmentation patch comprises a plurality of loops or pockets through which the flexible resilient member is disposed to couple the flexible resilient member with the tissue augmentation patch.

14. The method of claim 1, wherein the flexible resilient member defines a first end and a second end, the flexible resilient member further defining a closed curve such that the first is disposed adjacent to the second end, the second end and the first end being one of removably coupled or severably coupled together.

15. The method of claim 1, wherein the tissue augmentation patch comprises a one of a severable coupling or a removable coupling securing the tissue augmentation patch in the pre-deployment state, the method further including removing or severing the coupling.

16. The method of claim 15, wherein the flexible resilient member is configured to urge the tissue augmentation patch in the pre-deployment state towards the post-deployment state against the coupling such that one or severing or removing the coupling initiates movement of the tissue augmentation patch towards the post-deployment state.

17. The method of claim 1, wherein the flexible resilient member urges the tissue augmentation patch in the pre-deployment state towards the post-deployment state against the coupling such that the flexible resilient member in the pre-deployment state initiates movement of the tissue augmentation patch towards the post-deployment state.

18. The method of claim 1, wherein the tissue augmentation patch comprises at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, or fascia.

19. The method of claim 18, wherein the tissue augmentation patch comprises collagen.

20. A self-deploying soft tissue repair system, comprising:

a tissue augmentation patch having:

a first layer of material;

a tissue-facing surface; and a second surface opposed to the tissue-facing surface; and a flexible resilient member coupled to the tissue augmentation patch, wherein the tissue augmentation patch and the flexible resilient member together define a post-deployment state in which the tissue augmentation patch defines a first length, a first width, and a first thickness, wherein the tissue augmentation patch and the flexible resilient member together define a pre-deployment state in which the tissue augmentation patch defines a second length, a second width, and a second thickness, at least one of the second length or second width being smaller than the respective first length or width, and the second thickness being greater than the first thickness, wherein, in the pre-deployment state, at least a portion of the tissue augmentation patch is overlapping with a different portion of the tissue augmentation patch, wherein the self-deploying soft tissue repair system is moveable between the pre-deployment state and the post-deployment state, with moving the tissue augmentation patch from the pre-deployment to the post-deployment state includes twisting opposite ends of the patch in opposite directions such that the portion of the tissue augmentation patch and the different portion of the tissue augmentation patch is separated by a twisted region having a width that is smaller than a width of either the portion of the tissue augmentation patch and the different portion of the tissue augmentation patch, and folding one of the portion of the tissue augmentation patch or the different portion of the tissue augmentation patch relative to an other of one of the portion of the tissue augmentation patch and the different portion of the tissue augmentation patch about the twisted region to contact the portion of the tissue augmentation patch and the different portion of the tissue augmentation patch, and wherein, during a movement from the pre-deployment state towards the post-deployment state, the flexible resilient member is configured to complete the movement of the tissue augmentation patch to the post-deployment state.

21. The method of claim 1, wherein the width of the first portion and the second portion is substantially equal.

22. The method of claim 1, further comprising cutting the flexible resilient member.

23. The method of claim 22, further comprising removing the flexible resilient member from the self-deploying patch in the post-deployment state.

* * * * *